(12) United States Patent
Chen et al.

(10) Patent No.: US 10,465,161 B2
(45) Date of Patent: Nov. 5, 2019

(54) SCAFFOLD-FREE 3D CELL ASSEMBLY BASED ON PATTERNED HYDRODYNAMIC DRAG FORCE

(71) Applicant: The Board of Trustees of the Leland Stanford Junior University, Palo Alto, CA (US)

(72) Inventors: Pu Chen, Wuhan (CN); Utkan Demirci, Stanford, CA (US); Sinan Güven, Izmir (TR)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 309 days.

(21) Appl. No.: 15/519,101

(22) PCT Filed: Oct. 26, 2015

(86) PCT No.: PCT/US2015/057411
§ 371 (c)(1),
(2) Date: Apr. 14, 2017

(87) PCT Pub. No.: WO2016/069493
PCT Pub. Date: May 6, 2016

(65) Prior Publication Data
US 2017/0226473 A1    Aug. 10, 2017

Related U.S. Application Data

(60) Provisional application No. 62/085,023, filed on Nov. 26, 2014, provisional application No. 62/068,939, filed on Oct. 27, 2014.

(51) Int. Cl.
*C12N 5/00* (2006.01)
*C12N 5/071* (2010.01)
*C12M 3/00* (2006.01)
*C12M 1/42* (2006.01)

(52) U.S. Cl.
CPC ............. *C12N 5/0062* (2013.01); *C12M 3/00* (2013.01); *C12M 21/08* (2013.01); *C12M 35/04* (2013.01); *C12N 5/0671* (2013.01); *C12N 2502/28* (2013.01); *C12N 2503/00* (2013.01)

(58) Field of Classification Search
None
See application file for complete search history.

(56) References Cited

U.S. PATENT DOCUMENTS

2012/0141552 A1\* 6/2012 Dalecki ................ C12N 5/0062
424/400

OTHER PUBLICATIONS

Chen et al., "Microscale Assembly Directed by Liquid-Based Template", Advanced Materials, vol. 26, pp. 5936-5941. (Year: 2014).\*

\* cited by examiner

*Primary Examiner* — Michelle F. Paguio Frising
(74) *Attorney, Agent, or Firm* — Lumen Patent Firm

(57) ABSTRACT

A method of making a multi-layer patterned cell assembly is provided. A cell suspension liquid solution containing cells is loaded into a liquid-carrier chamber. The cells in the cell suspension liquid solution are let to settle down to the bottom of the chamber. Once the cells in the cell suspension liquid solution have gravitationally settled down to the bottom of the chamber, a hydrodynamic drag force is applied by using a vibration generator with a frequency and acceleration to the cells at the bottom of the chamber. The frequency and acceleration are designed to drag the settled cells into a three-dimensional pattern to form a multi-layer three-dimensional patterned cell assembly. The formed multi-layer three- dimensional patterned cell assembly can be transferred from the liquid-carrier chamber to an incubator to form a tissue culture. The bioengineered construct can be implanted for tissue engineering or other medical applications.

5 Claims, 31 Drawing Sheets

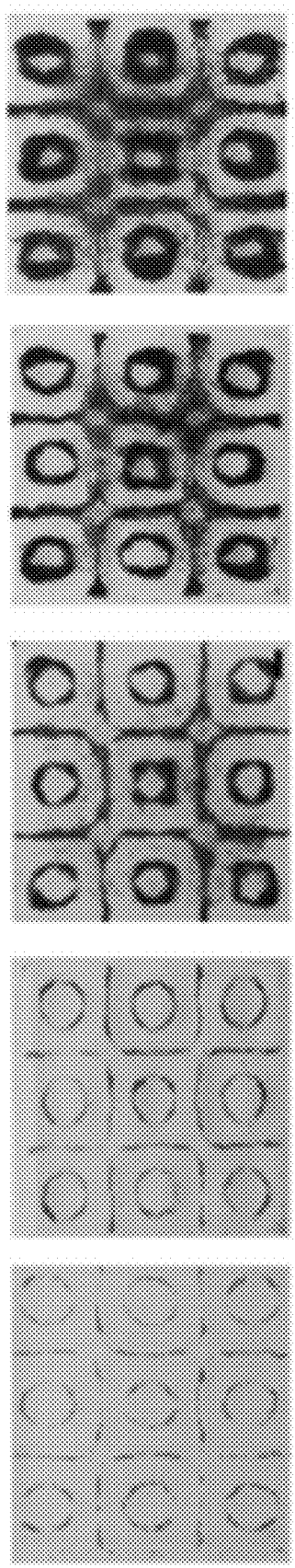
FIG. 7A 0.8 mg
FIG. 7B 2.4 mg
FIG. 7C 8.4 mg
FIG. 7D 16.8 mg
FIG. 7E 25.2 mg

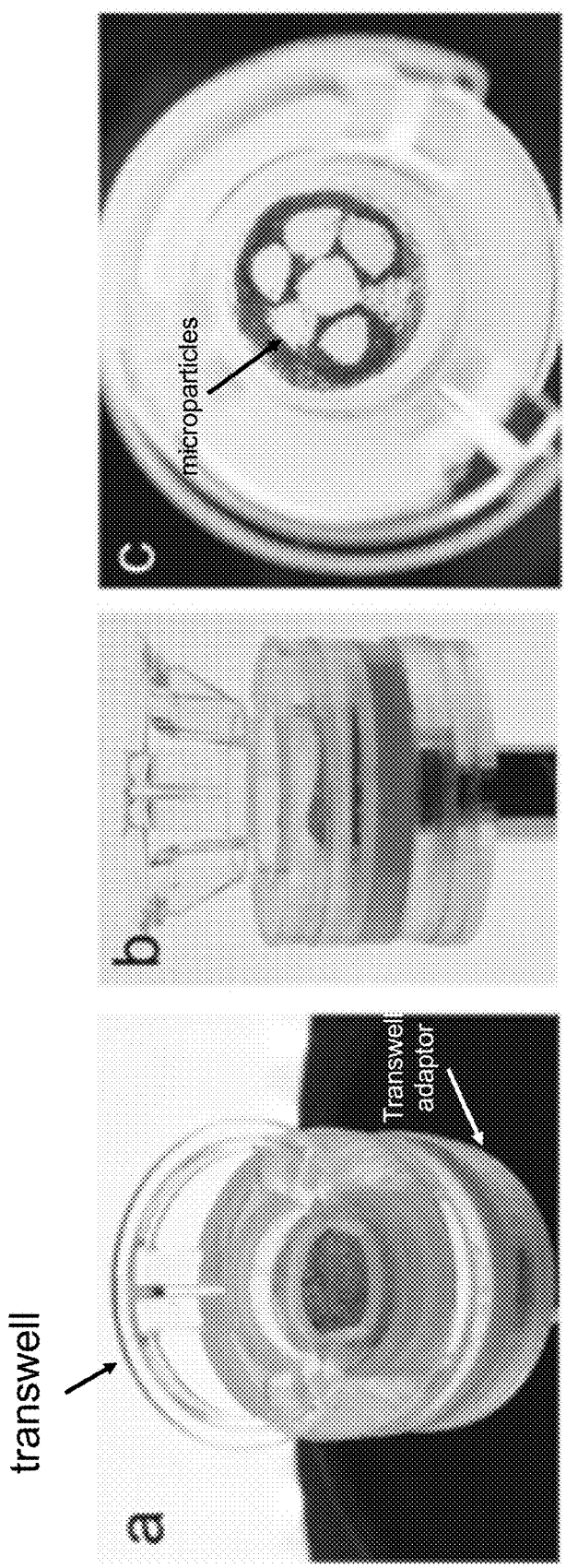

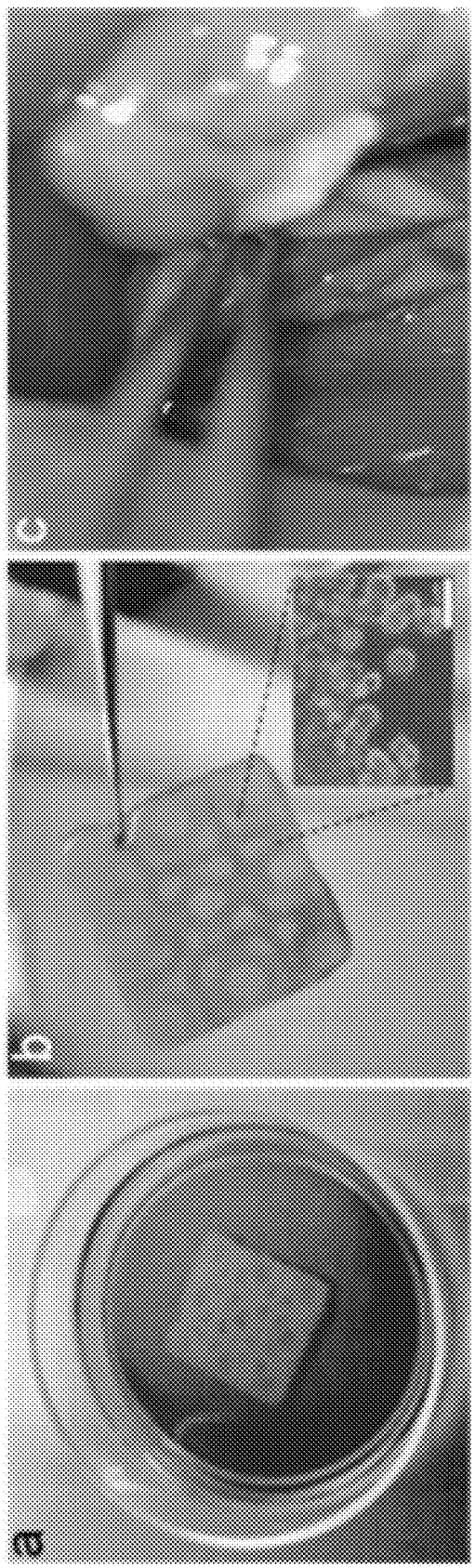

FIG. 15B Bright field

FIG. 15D Phalloidin

FIG. 15A Merged

FIG. 15C DAPI

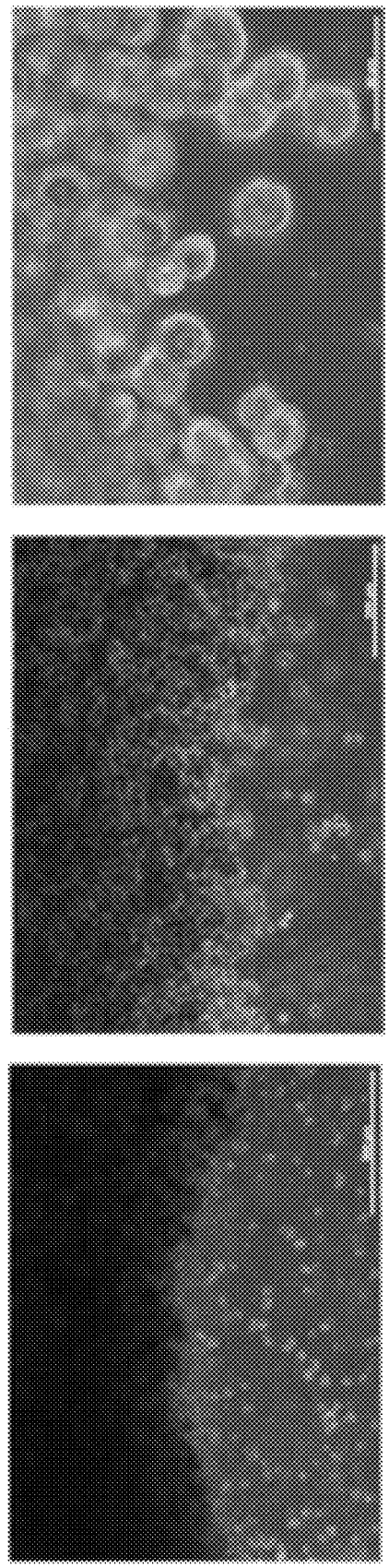

FIGs. 24A-T

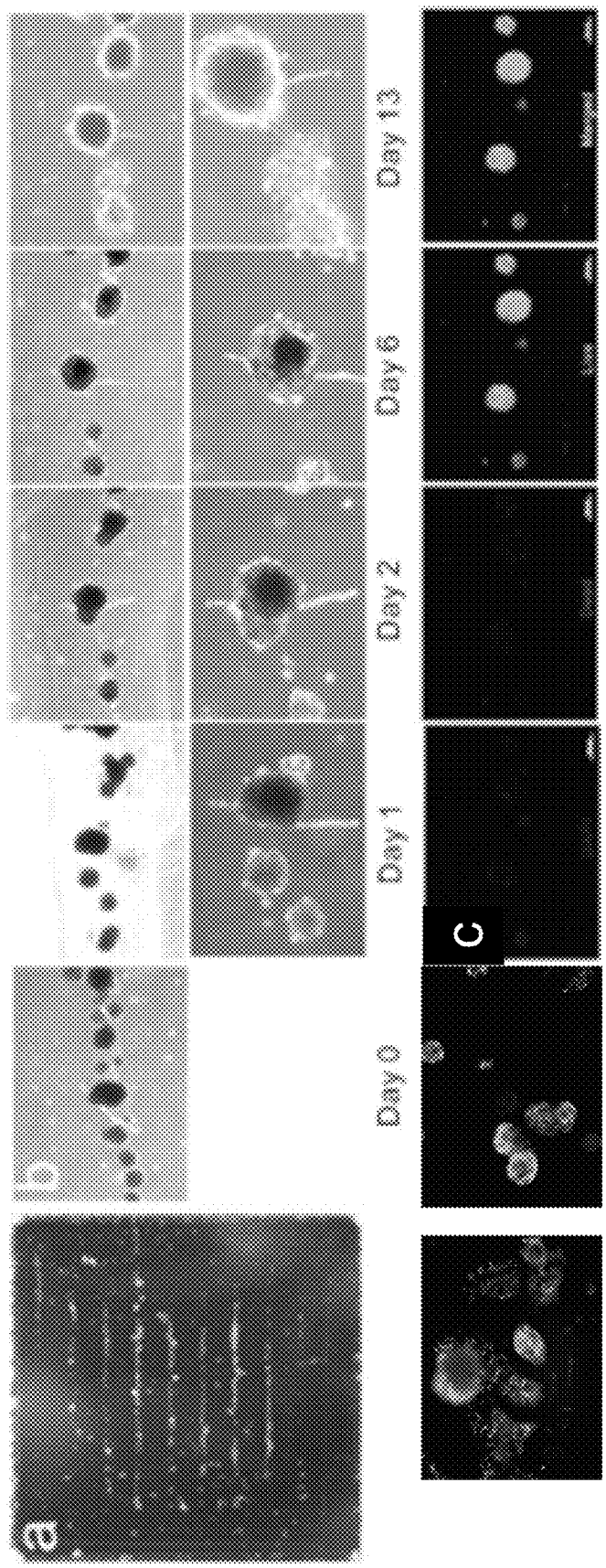
FIGs. 26A-C

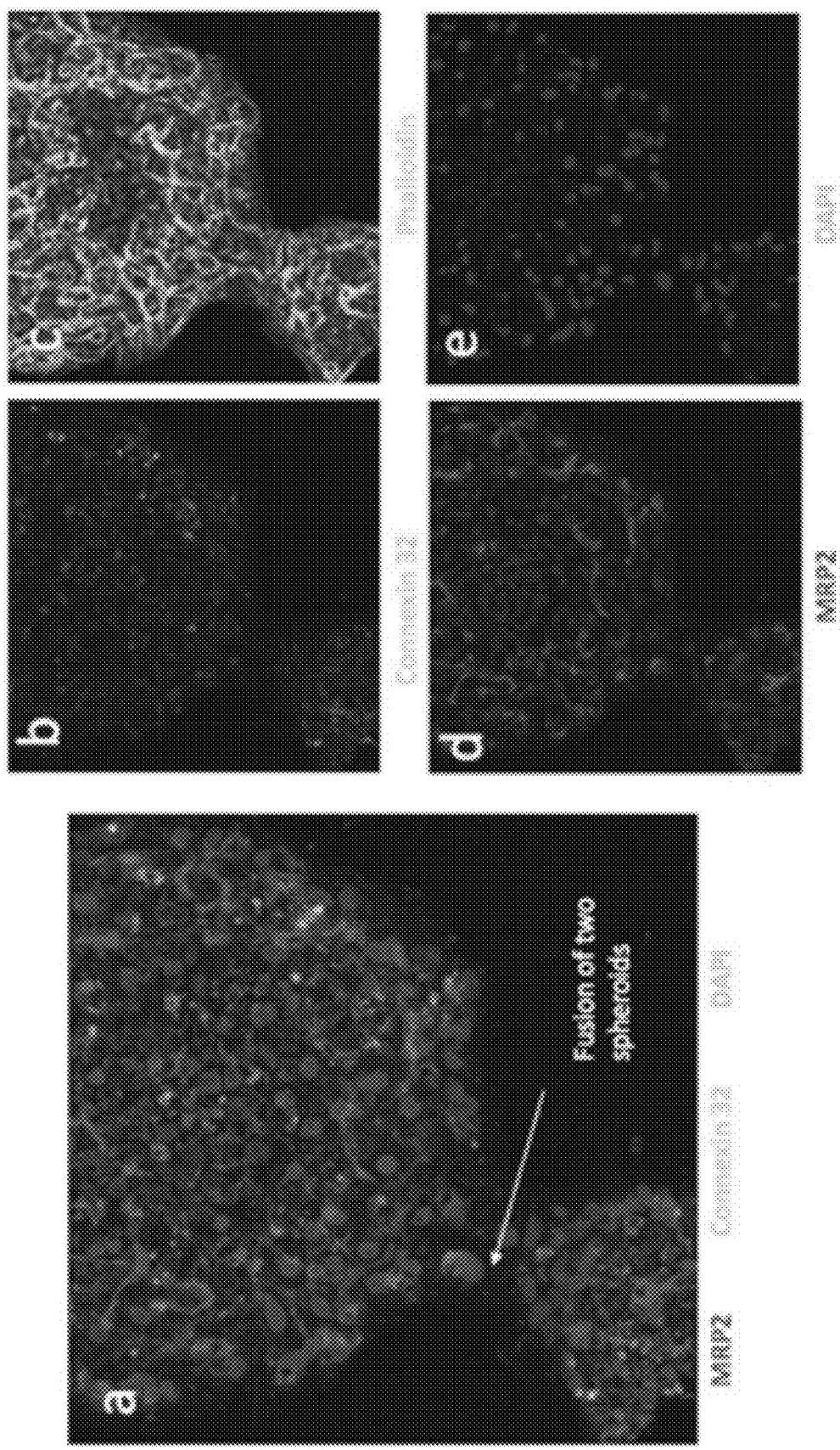
FIGs. 27A-E

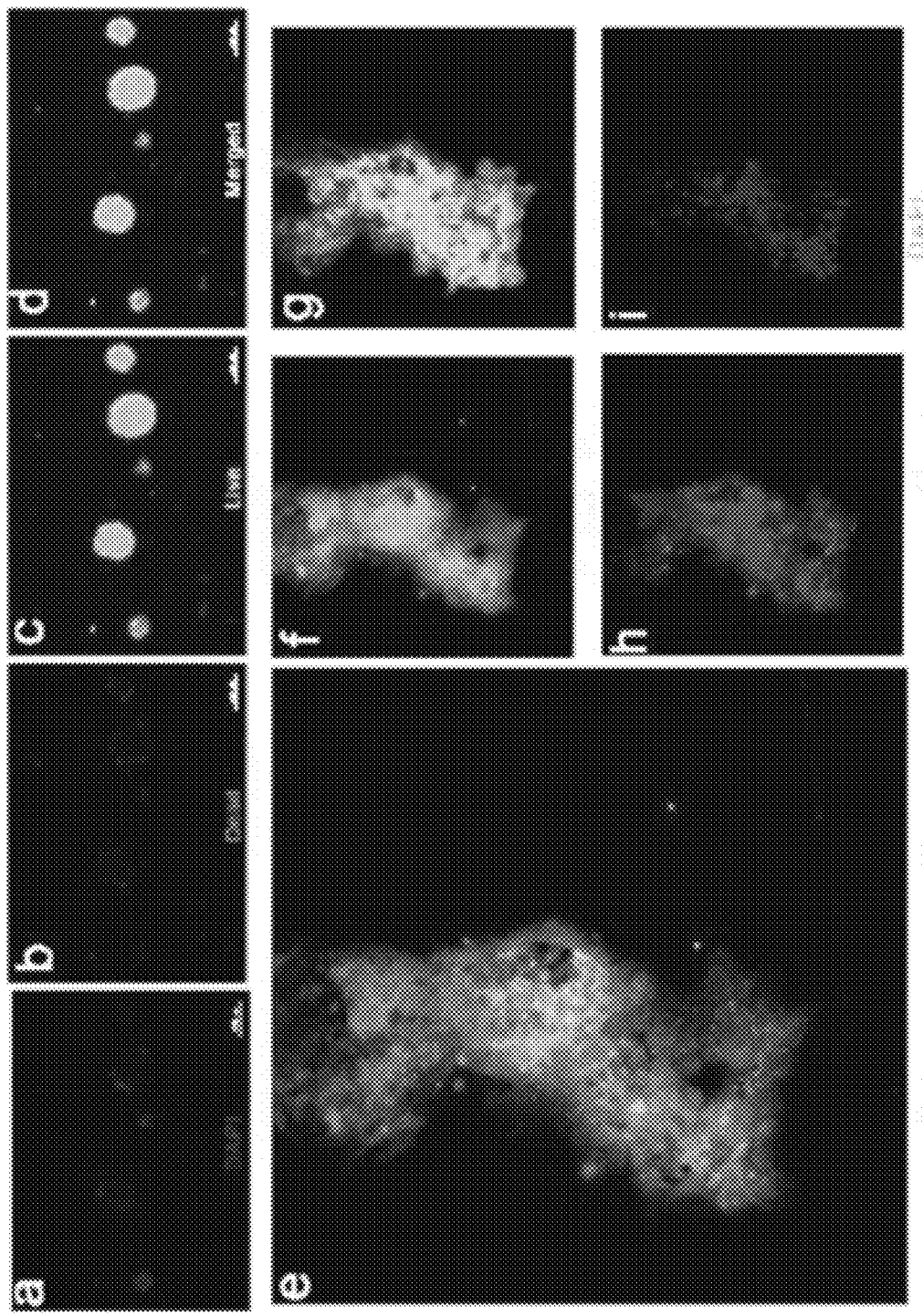
FIGs. 28A-I

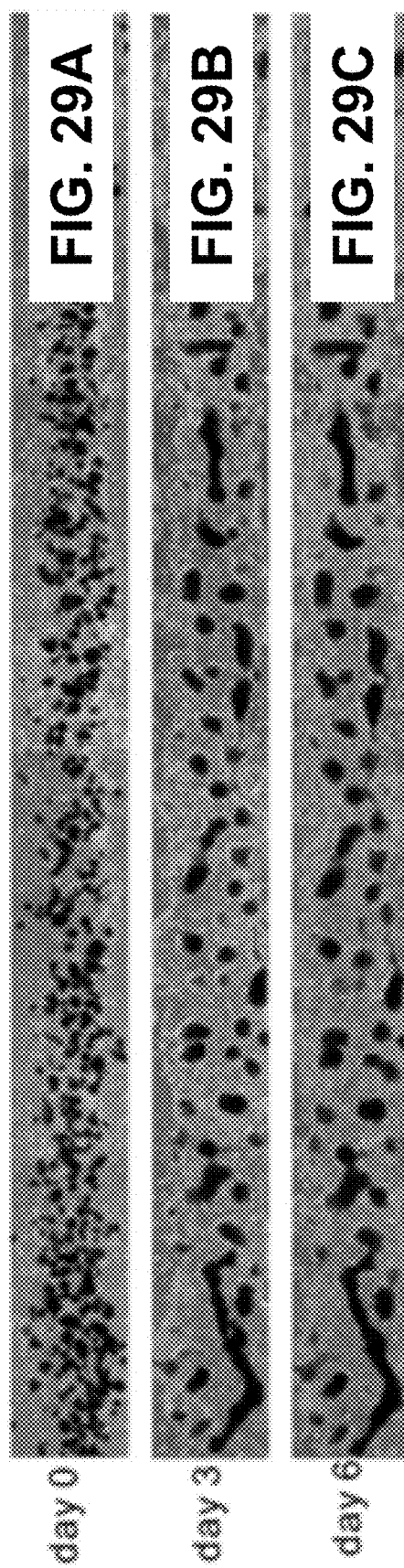

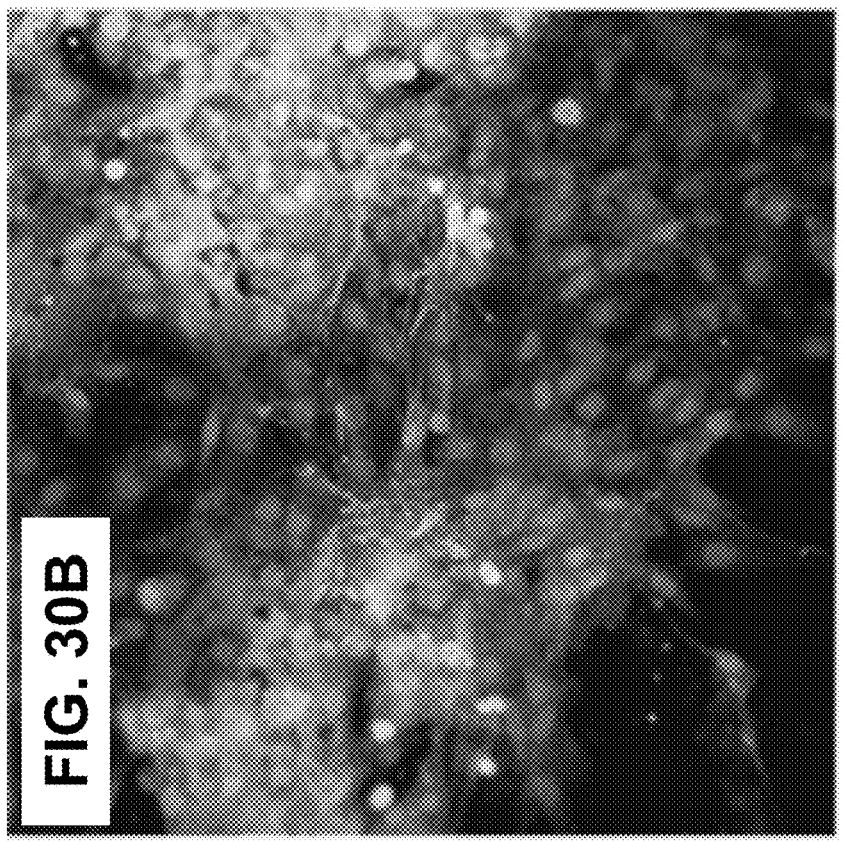
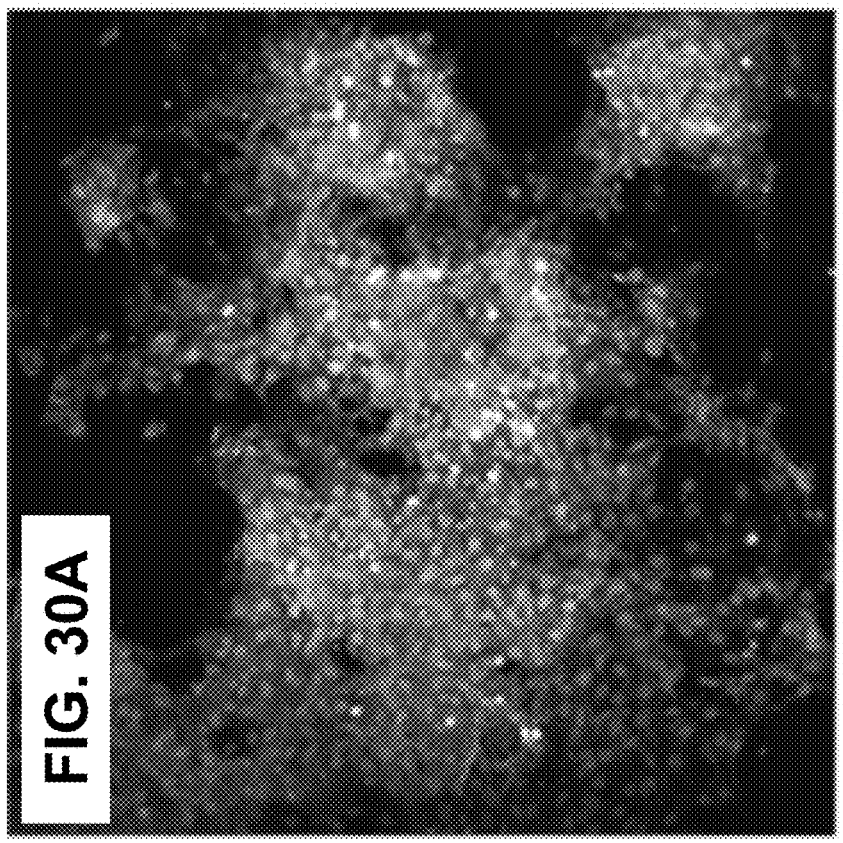

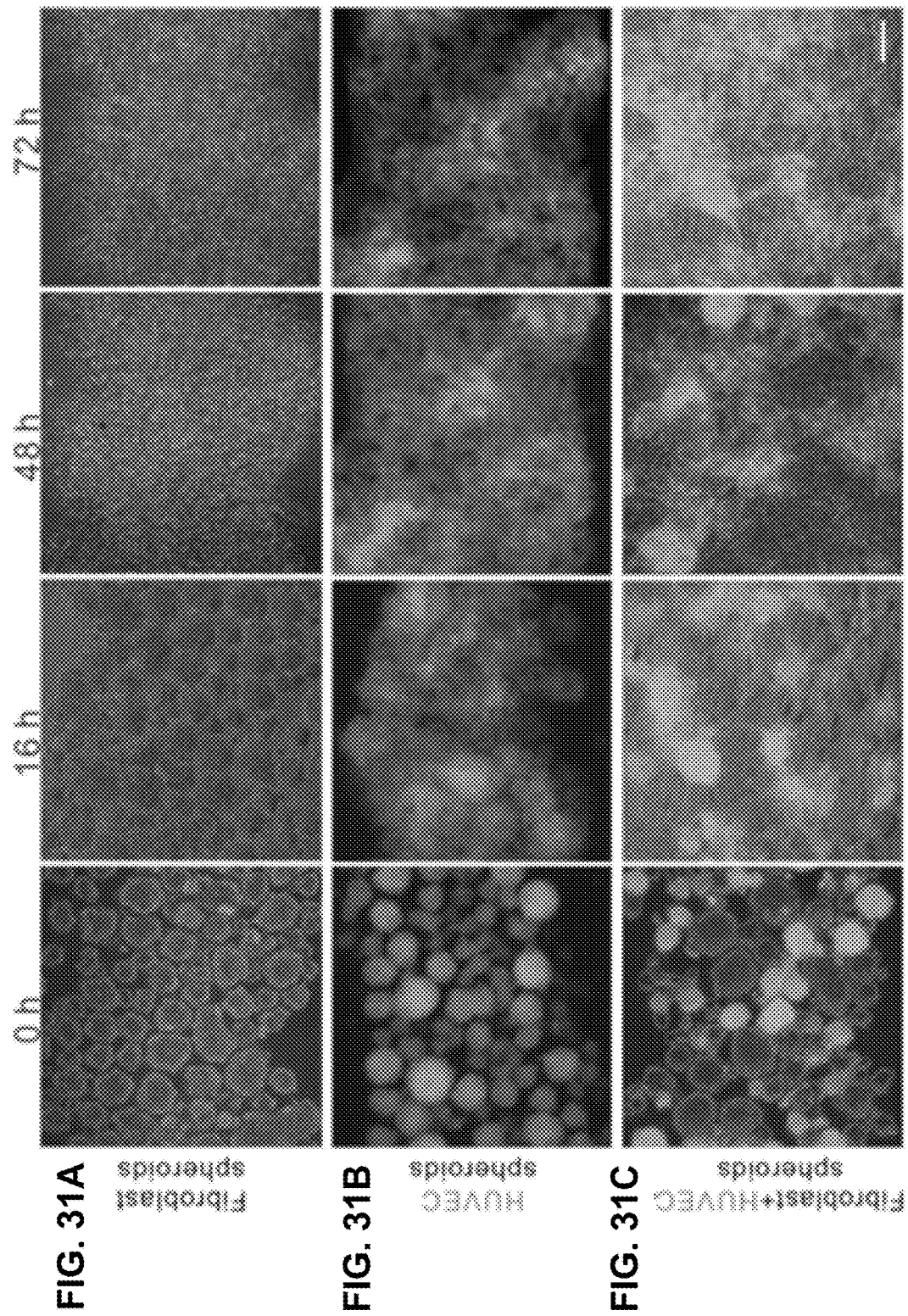

SCAFFOLD-FREE 3D CELL ASSEMBLY BASED ON PATTERNED HYDRODYNAMIC DRAG FORCE

FIELD OF THE INVENTION

This invention relates to liquid-based patterning for 3D cell assembly.

BACKGROUND OF THE INVENTION

The effectiveness and high cost of current drug screening approaches are two major factors that challenge the pharmaceutical industry. The cost of bringing a single drug to the market is now estimated at about 1 billion dollars. 40 to 70% of this total development cost is invested in the pre-clinical and clinical stages. This high cost is due to the high number of failed drugs where two dominant factors for failure are lack of efficacy, and toxicity.

In vitro organ models hold a great promise as more physiological relevant platforms in drug screening than traditional approaches based on animal tests. Therefore, the ability to generate human tissue mimicries that represent basic tissue functional structures, such as hepatic acinus in the liver, nephrons in the kidney, is of benefit for drug screening as well as diverse applications in tissue engineering and regenerative medicine.

Despite the intense research on generating such platforms, a number of challenges constrains the bioengineering of organ models for practical applications including (1) organization of cells and their surrounding microenvironments with microscale resolution in the bioengineered tissue functional units; (2) sufficient vascularization inside tissue functional units for minimization of necrosis and loss of function; (3) need for high throughput generation of complex 3D repeating units.

Many tissues in the human body are composed of densely-packed cells and low extracellular matrix (ECM). For example, liver tissue, hepatocytes and endothelial cells constitute most of liver wet weight while ECM contributes approximately 0.5-3% of the total wet weight. The cell proximity is important to retain hepatocyte viability and form liver-specific functions.

Currently most of the methods developed for in vitro formation of liver tissue utilize scaffolds for cell homing. Scaffolds used in liver tissue engineering dramatically decrease cell-cell interactions that are critical for maintaining the functionality of the hepatocytes. Accordingly, tissue-engineering technologies mimicking cell-packing density similar to the native tissue are required.

SUMMARY OF THE INVENTION

The present invention provides technology to generate scaffold-free, vascularized three-dimensional (3D) organ mimicry tissue functional units by bringing together microscale assembly, biomaterials and tissue engineering principles. In particular this invention provides a technology to engineer a broadly applicable scaffold-free platform, generating spatially organized and functionalized tissue constructs for high-throughput drug screening. Our scope is to generate vascularized tissue subunits with microscale control over cell distribution and architecture. We envision that parenchymal and non-parenchymal cell interactions in a 3D scaffold-free assembly will stabilize and enhance hepatic function and recapitulate the human physiological responses to drugs. In one embodiment, we developed a liquid-based patterning technology, which can hierarchically coordinate parenchymal cells (hepatocytes) and non-parenchymal cells (stromal and endothelial cell) types in predefined structures.

The ability to generate 3D tissues with high-cell packing density and predefined complex structure units is of benefit for diverse tissue engineering applications in therapeutics, diagnostics and drug screening.

Although many approaches have been demonstrated for spatial organization of cells with cell-carriers, such as cell-encapsulating hydrogels and cell-seeded micro-carrier beads, these approaches can't achieve similar cell packing density with native tissue due to large ratio of cell scaffold in the carriers. Methods such as hanging drop techniques, to create high-density tissue constructs take up a week to reach a cellular 3D assembly and can only generate spheroid-shaped 3D structure.

The embodiments of this invention provide a bottom-up approach for scaffold-free 3D cell assembly to generate repeating and symmetric cellular structures with cell packing density similar to the scaffold-based tissue engineering methods and cytocompatibility.

In one exemplary embodiment, the invention can be described as a method of making a multi-layer patterned cell assembly according to the following steps. A liquid-carrier chamber defining a bottom of the chamber is provided. A cell suspension liquid solution containing cells is loaded into the liquid-carrier chamber. The cells in the cell suspension liquid solution are let to settle down to the bottom of the chamber. Once it has been determined that the cells in the cell suspension liquid solution have gravitationally settled down to the bottom of the chamber, a hydrodynamic drag force is applied by using a vibration generator with a frequency and acceleration to the cells at the bottom of the chamber. The frequency and acceleration are designed to drag the settled cells into a three-dimensional pattern to form a multi-layer three-dimensional patterned cell assembly. The frequency is defined in a range of 1 Hz-10,000 Hz and the acceleration is defined in a range of [0.01 m/s$^2$-5000 m/s$^2$]. Two types of particles can be assembled into complementary patterns according to their size within the multi-layer three-dimensional patterned cell assembly. The formed multi-layer three-dimensional patterned cell assembly can be transferred from the liquid-carrier chamber to an incubator to form a tissue culture.

As an typical example, we differentiate RMA iPS cell lines in vitro for 9 days using Cambridge protocol. We harvested these iPS cells and mixed iPS derived hepatocytes with human umbilical vein endothelial cells (HUVECs) with a ratio of 10:7. We prepared fibrinogen solution with a concentration of 8 mg/mL. We loaded the cell mixture in the fibrinogen solution in the liquid carrier chamber. We assembled this cell mixture into a circular and cross shapes on the substrate of the liquid carrier chamber (FIG. 14C). The assembled structure is immobilized by adding thrombin solution. We differentiate iPS derived hepatocytes in the construct up to DIV 33. This construct was transplanted to mice and generated very high albumin secretion (around 1 µg human albumin/mL blood/1 M cells) after one week transplant.

The liquid carrier chamber can be a customized device or standard tissue culture multiwall plate, a transwell plate, a Petri dish or other liquid containers.

BRIEF DESCRIPTION OF THE DRAWINGS

FIG. 5A shows force potential at the liquid thickness of 1.67 mm. FIG. 5B shows force potential at the cross-section of liquid layer. Simulation results are obtained from the equation(s) described herein. Particles fill the substrate from the regions with lower potential to the regions with higher force potential.

FIGS. 7A-E show according to an exemplary embodiment of the invention particle number effects on the assembly. Investigations were performed of assembly under different particle concentration. Assembly structure becomes multilayer as the number of particle increases in the chamber.

FIG. 8A shows simulation results of particle density effect on assembly pattern. When maximum force potential is positive, particles are assembled under the nodal region of the standing waves. When maximum force potential is negative, particles are assembled under the antinode region of the standing waves. Dashed line indicates force potential is equal to zero. FIG. 8B shows experimental results of particle assembly with different buoyant density. Particles with small buoyant density are assembled under nodal regions of Faraday waves. Particles with large buoyant density are assembled under antinode regions of Faraday waves.

FIG. 9A shows particle size effect on assembly. When maximum force potential is positive, particles are assembled under the nodal region of the standing waves. When maximum force potential is negative, particles are assembled under the antinode region of the standing waves. FIG. 9B shows experimental results of assembly with different particle sizes. Particles with small size are assembled under nodal regions of Faraday waves. Particles with large size are assembled under antinode regions of Faraday waves.

FIG. 11A shows maximum force potential under varied liquid thickness and wavelengths. When maxim force potential is positive, particles are assembled on the nodal lines of standing waves; while maxim force potential is negative, particles are assembled on the antinodes of the standing waves. FIG. 11B shows particles (100 μm in diameter; buoyant density, 1.02 g/mL) are assembled under nodal regions of Faraday waves at the low frequency. Particles are assembled under antinode regions of Faraday waves at the high frequency.

FIGS. 12A-C show according to an exemplary embodiment of the invention an alternative liquid-carrier chamber. Here the assembly in a trans-well chamber is mounted on the holder. FIG. 12A shows initial state. FIG. 12B shows a side view. FIG. 12C shows up-down view. After assembly, assembled cells in the trans-well can be easily transferred to the multi-well plate for tissue culture. The permeable supports allow sufficient nutrient/waste exchange.

FIGS. 14A-C show according to an exemplary embodiment of the invention the immobilization of assembled structure and retrieval of an assembled structure. Hepatocytes were assembled in a mixture solution of fibrinogen (final concentration, 8 mg/mL) and thrombin (final concentration, 0.5 IU/mL). After assembly, the pattern was immobilized in the fibrin hydrogel by crosslinking of fibrinogen with thrombin. The crosslink time depends on the concentration of thrombin. The stiffness of the fibrin hydrogel depends on the concentration of fibrinogen. We used fibrinogen at a final concentration of 8 mg/mL and thrombin at a final concentration of 0.5 IU /mL. Gelation was completed within 15 min. After gelation, the fibrin hydrogel containing cells were transferred a Petri dish with tissue culture medium for tissue culture and maturation. After 22-day culture in vitro using Cambridge protocol, fibrin construct containing iPS-hepatocytes were transplanted into a mouse. Transplant of hepatocyte encapsulating fibrin hydrogel construct into a mouse. FIG. 14A shows in vitro 3D culture of assembled hepatocytes in the fibrin hydrogel construct. FIG. 14B shows 3D patterned hepatocytes in fibrin hydrogel. FIG. 14C shows transplanting the iPS hepatocyte encapsulating hydrogel in a mouse.

FIGS. 15A-B show according to an exemplary embodiment of the invention high cell-packing density. FIG. 15A shows a merged image of DAPI and Phalloidin. FIG. 15B shows a bright field Cell density~$1 \times 10^8$ cells mL$^{-1}$. FIG. 15C shows DAPI staining FIG. 15D shows Phalloidin staining. Results indicate formation of multilayer packed cell structure.

FIGS. 16A-C show according to an exemplary embodiment of the invention edge of an assembled region. The edge of an assembled region is sharp and clear contrasted with the unassembled region. FIGS. 16A-C each show a different magnification.

FIG. 23A shows a schematic of formation of cell spheroids using low adhesion plate. FIG. 23B shows a photo of generated cell spheroids. FIG. 23C shows a schematic of spheroid assembly using hydrodynamic drag force created by standing waves. FIG. 23D shows a photo of spheroid assembly under standing waves.

FIGS. 24A-T show according to an exemplary embodiment of the invention diverse patterns of assembled spheroids hydrodynamic drag force patterning of fibroblast cell spheroids into different patterns. FIGS. 24A-S show cell spheroid patterns are generated under different frequencies. FIG. 24T shows control group without patterning. Scale bar is 2 mm. Cell spheroids are patterned at the bottom of the chamber. Scale bar is 2 mm.

FIGS. 26A-C show according to an exemplary embodiment of the invention an assembly of hepatocyte spheroids (primary cells with limited proliferation). FIG. 26A shows a patterned hepatocyte spheroids are cross-linked in 10 mg mL$^{-1}$ fibrinogen (500 µL) mixed with 0.31 IU mL$^{-1}$ thrombin (150 µL). Gelation was completed within 15 min and transferred into 30 mm Petri dish supplemented with cell culture medium. Cell spheroids fused into large microtissues. FIG. 26A shows a time lapse of tissue culture. FIG. 26C shows Live/dead staining. FIG. 26B shows CMFDA staining, CMFDA assays on co-cultured hepatocytes CMFDA assays. Green area (shown as grey scale) between hepatocytes indicate formation of bile canaliculi, FIGS. 27A-E show according to an exemplary embodiment of the invention immunostaining of human hepatocyte microtissue on day 13 Immunostaining of assembled hepatocyte spheroids. FIG. 27A shows merged images of immunostaining. FIG. 27B shows Connexin 32. FIG. 27C shows Phalloidin. FIG. 27D shows MRP2 indicate formation of Canaliculi. FIG. 27A shows DAPI.

FIGS. 28A-I show according to an exemplary embodiment of the invention immunostaining of hepatocyte microtissues—day 13. FIGS. 28A-D show live dead assays on patterned hepatocyte spheroids in day 7. FIGS. 28E-I show examples of immunostaining of fused hepatocyte spheroids. FIG. 28E shows a merged image of Connexin 32 and Collagen IV. FIG. 28F shows a Connexin 32. FIG. 28G shows Phalloidin. FIG. 28H shows Collagen. FIG. 28I shows DAPI.

FIGS. 29A-C show according to an exemplary embodiment of the invention assembly of hepatocyte spheroids with fibroblast cells at different days. Hepatocyte spheroids were mixed with NIH 3T3 fibroblast cells and HUVECs cells with a cell ratio of 10:1:4. Cells and spheroids were patterned by hydrodynamic drag force. The pattern were immobilized in 10 mg mL$^{-1}$ fibrinogen (500 µL) mixed with 0.48 IU mL$^{-1}$ thrombin (150 µL). Hydrogel was fully chemically cross-linked within 15 min and transferred into 30 mm Petri dish supplemented with cell culture medium. Dark regions indicate hepatocyte spheroids and microtissues, while bright regions indicate NIH 3T3 fibroblast cells.

FIGS. 30A-B show according to an exemplary embodiment of the invention immunostaining of engineered hepatic tissue mimics on the day 11 and indicate formation of bile canaliculi and gap junctions in the bioengineered 3D microtissues.

FIGS. 31A-C show according to an exemplary embodiment of the invention fibroblast spheroids (FIG. 31A), GFP-HUVEC spheroids (FIG. 31B), and 1:1 mixture of fibroblast and GFP-HUVEC spheroids were assembled separately (FIG. 31C). Spheroid fusion was recorded at t=0, 16, 48, and 72 h. Individual cell spheroids at 0 h gradually start to fuse at 16 h. At t=72 h spheroids at all conditions are totally fused. Images do not represent identical zones over time. Scale bars: 100 µm.

DETAILED DESCRIPTION

Setup

Figure 1:
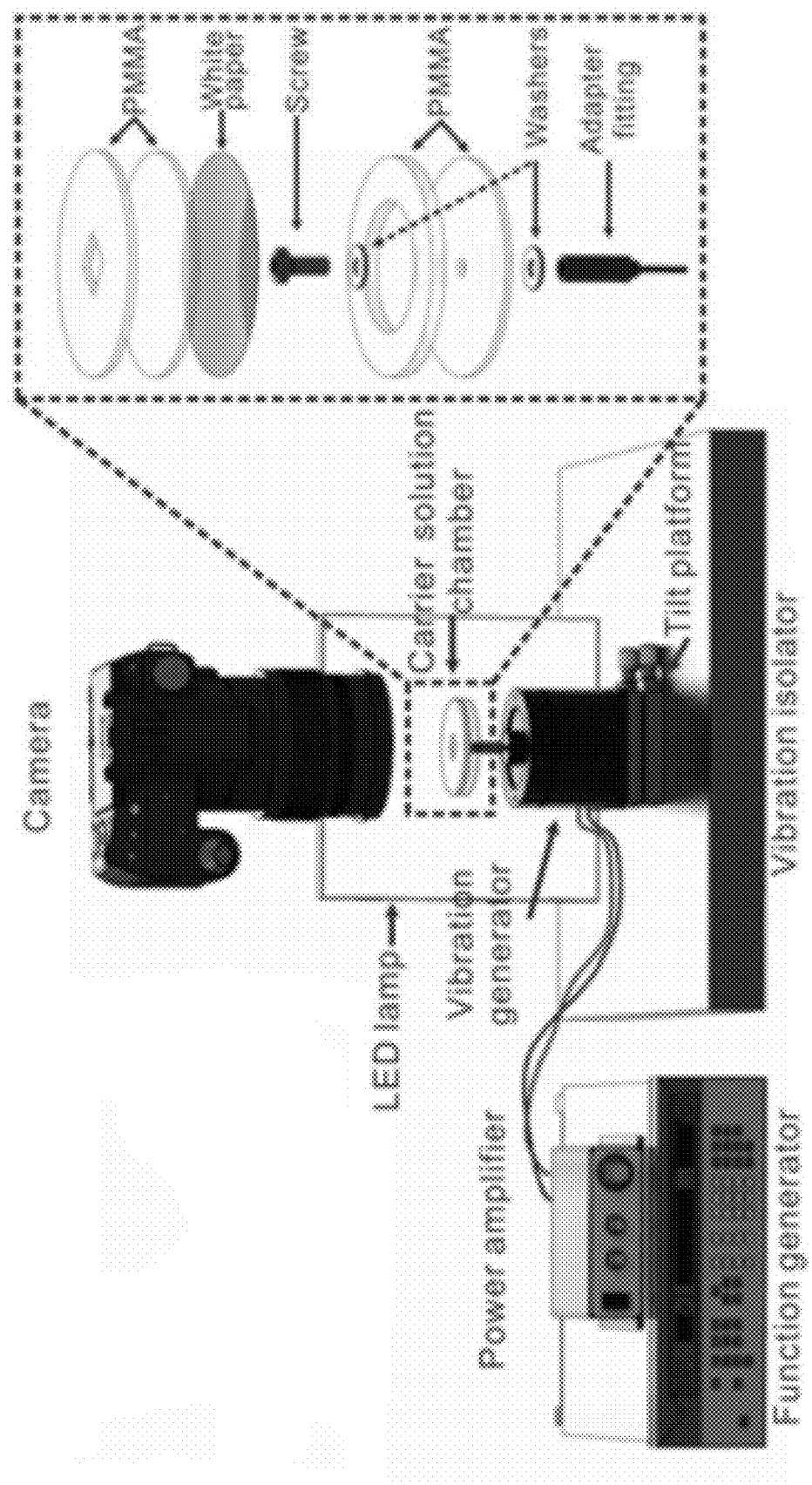
FIG. 1 shows according to an exemplary embodiment of the invention a schematic of the device setup. Right insert is an example of a device assembly.
Figure 2:
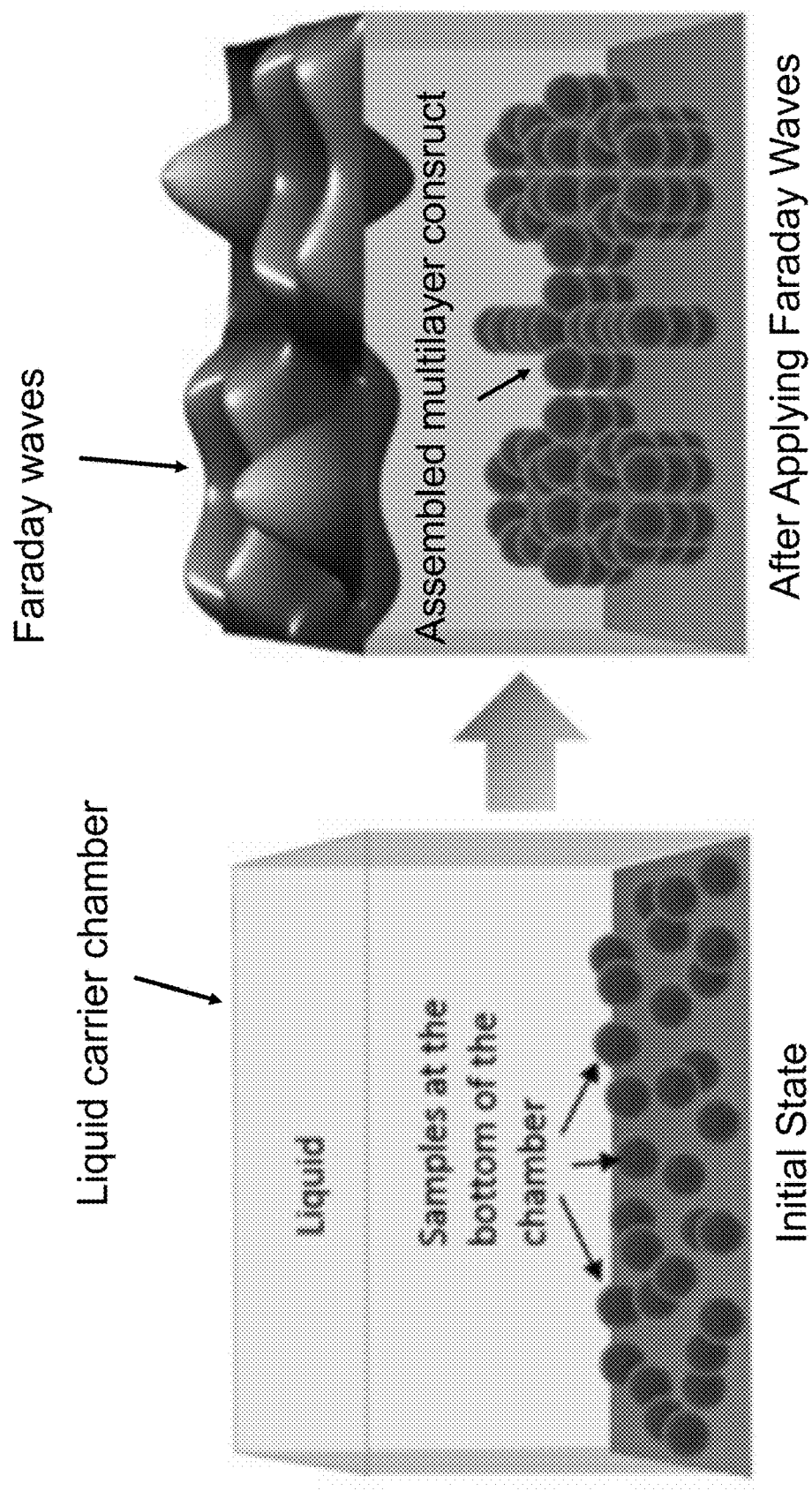
FIG. 2 shows according to an exemplary embodiment of the invention a process of assembly inside liquid. Random particles inside liquid on the substrate of liquid-carrier chamber are assembled into multilayer patterns by applying patterned hydrodynamic drag force created by Faraday waves.
Figure 3:
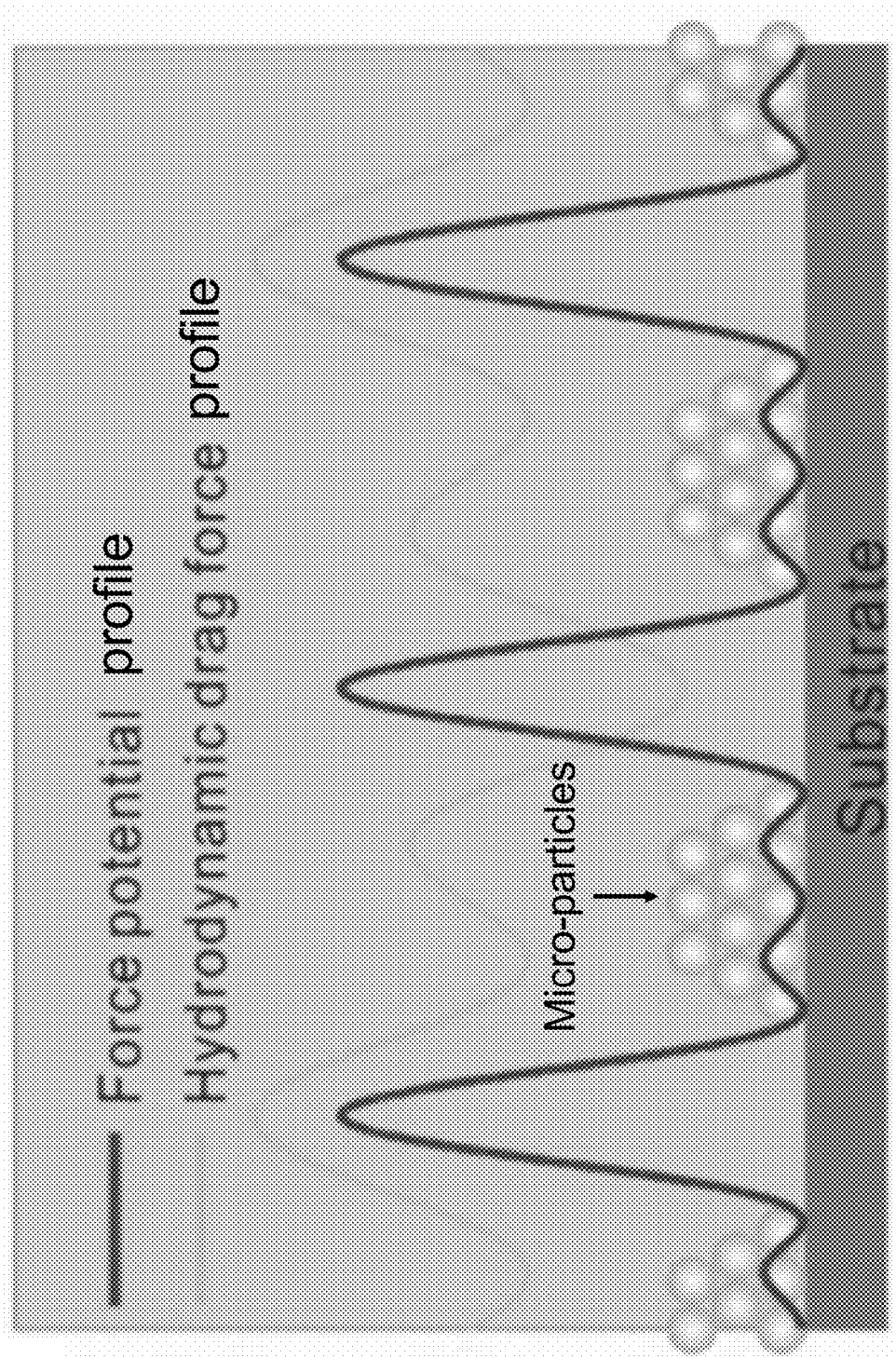
FIG. 3 shows according to an exemplary embodiment of the invention a principle demonstration of hydrodynamic drag force and corresponding force potential. Particles are packed at the region with the lowest force potential.
Figure 4:
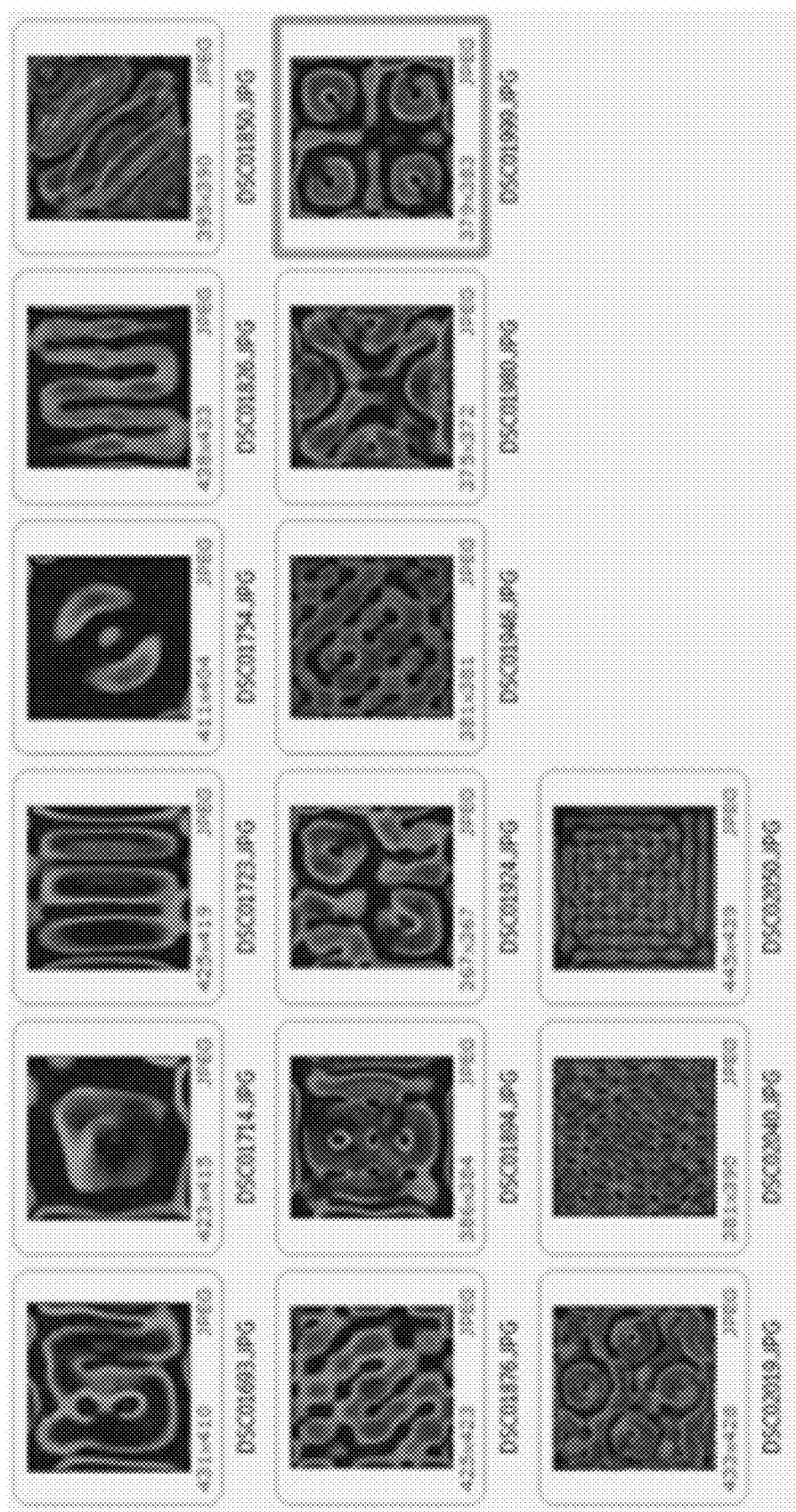
FIG. 4 shows according to exemplary embodiment of the invention with faraday waves (each of the reflection photos), which were obtained by adjusting frequency and acceleration.
Figure 5B:
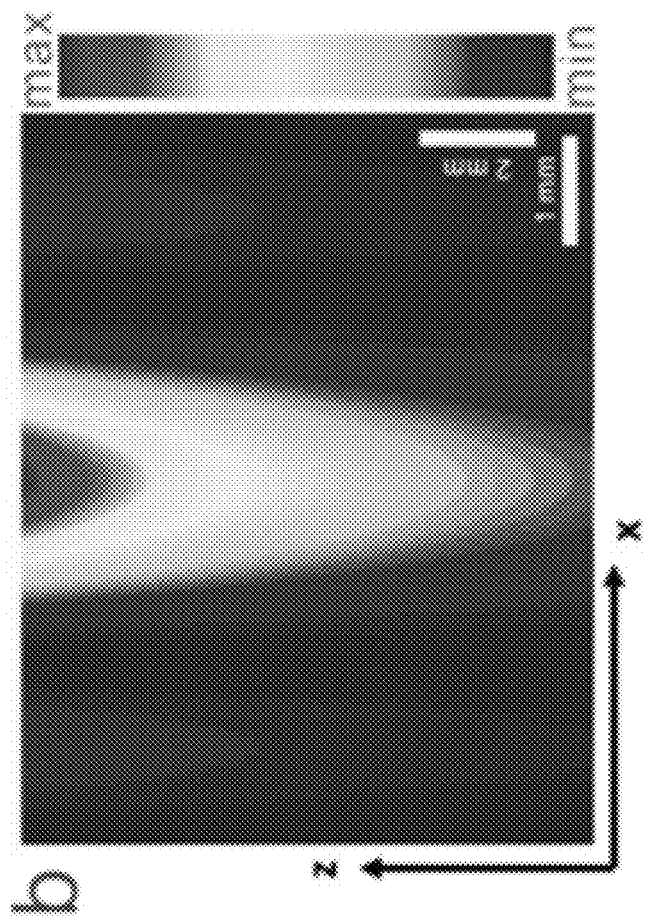
FIGS. 5A-B show according to an exemplary embodiment of the invention numerical simulations of force potential of interaction between particles and hydrodynamic drag force.
Figure 5A:
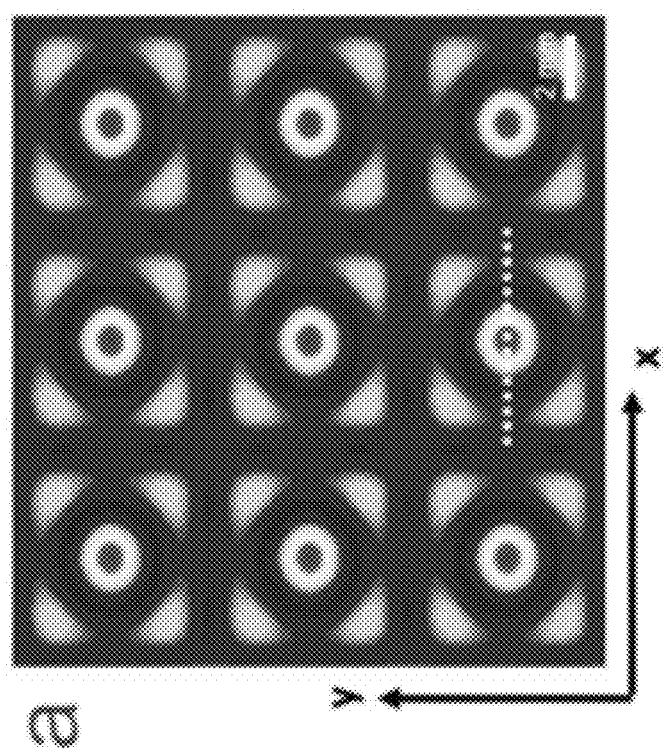
Figure 6:
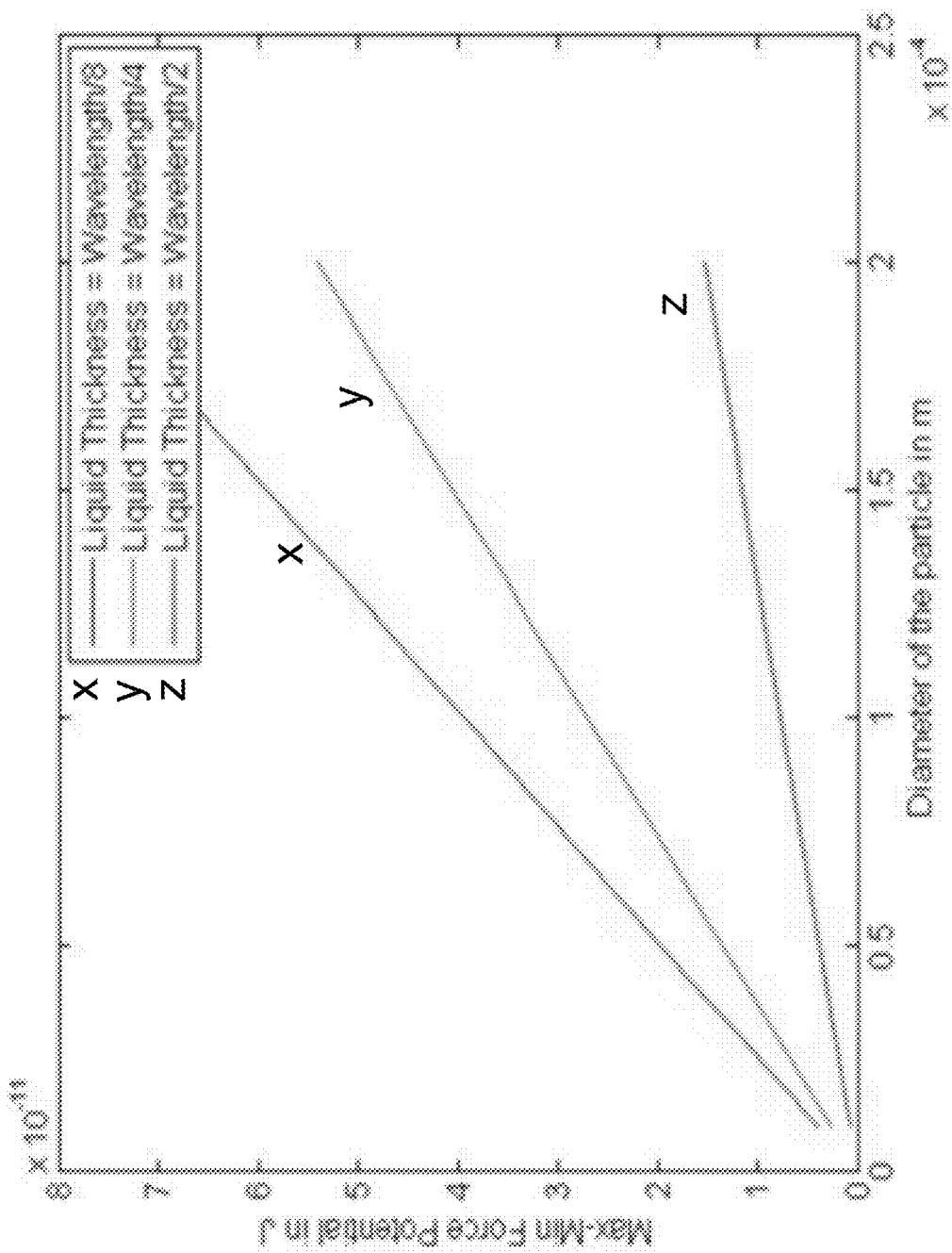
FIG. 6 shows according to an exemplary embodiment of the invention liquid thickness effect on force potential. Difference between force potential max and min decreases as liquid thickness increases in the chamber, which means that the particles become more dispersed, which the liquid thickness increases.
Figure 8A:
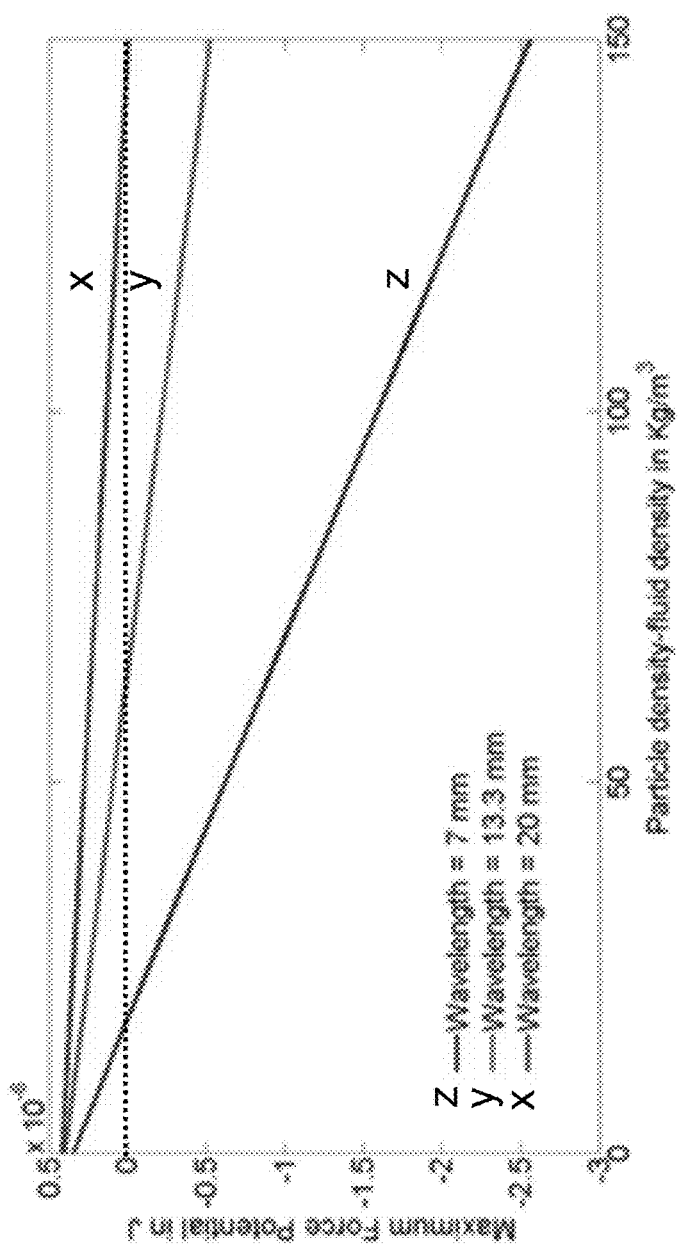
FIGS. 8A-B show according to an exemplary embodiment of the invention particle density effect on assembly
Figure 8B:
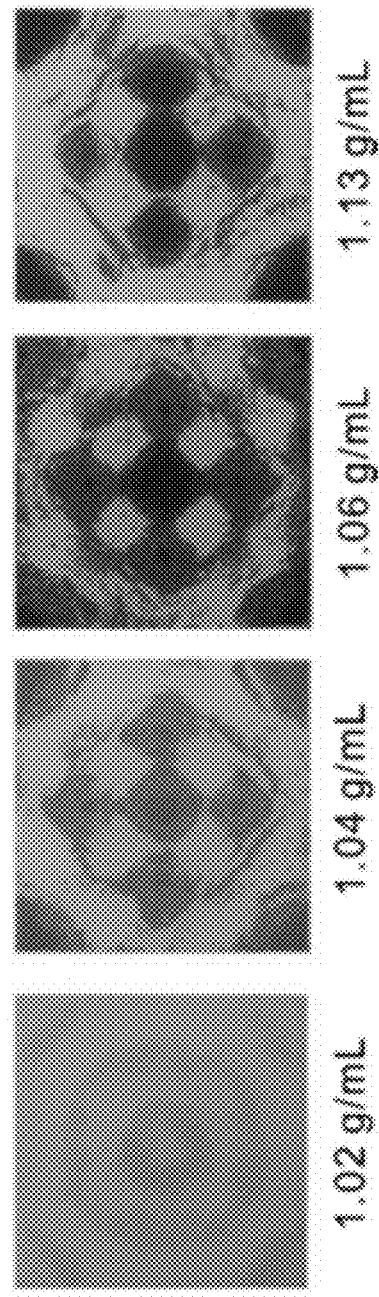
Figures 9A, 9B:
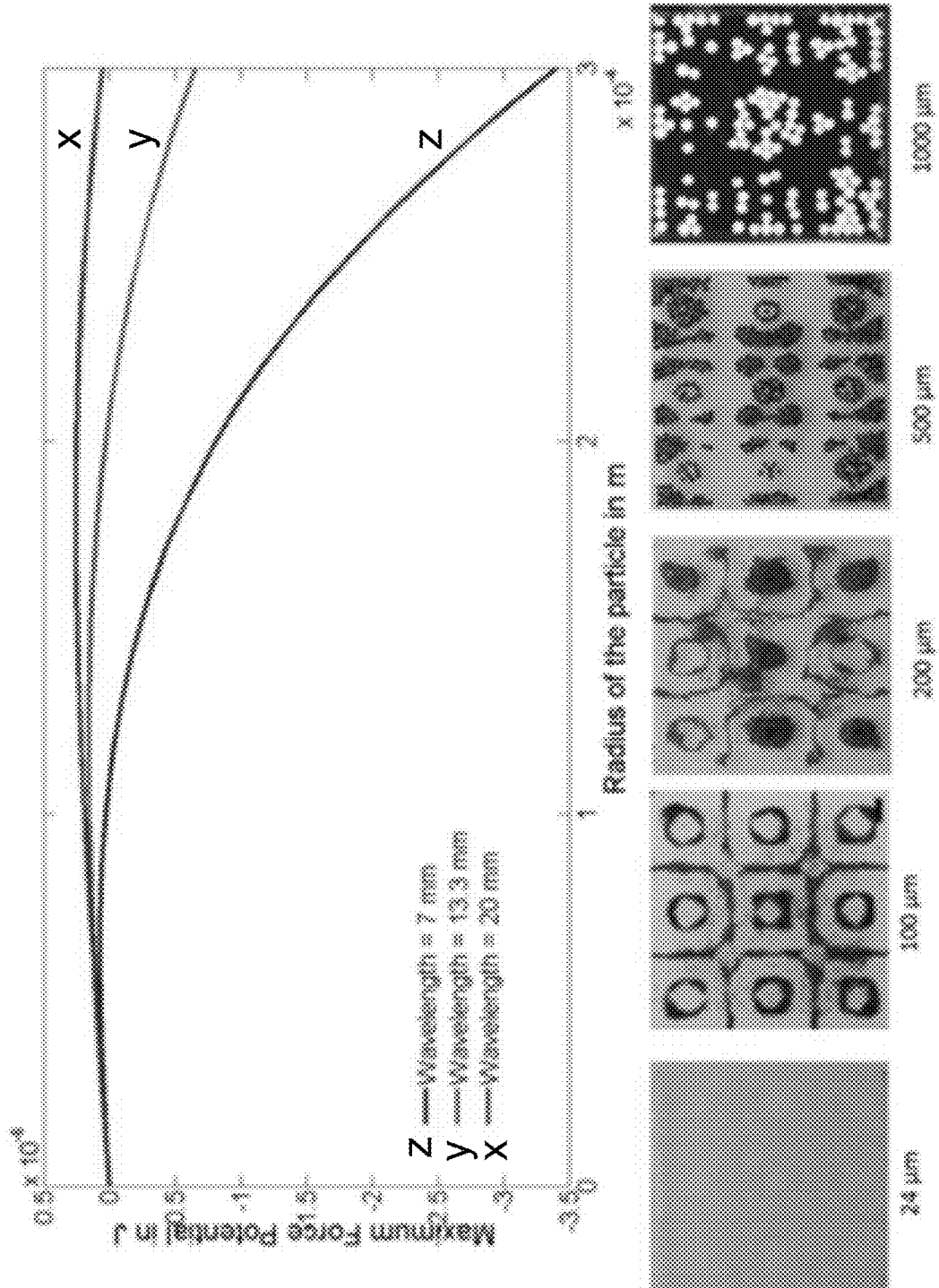
FIGS. 9A-B show according to an exemplary embodiment of the invention particle size effect on the assembly.
Figure 10:
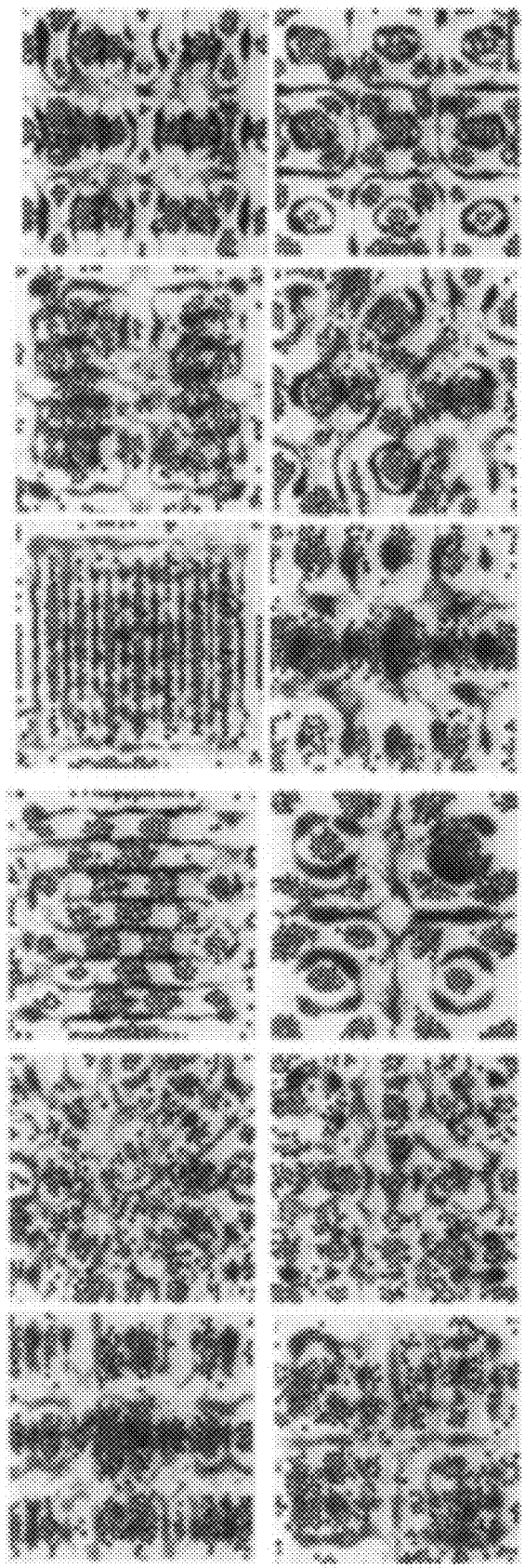
FIG. 10 shows according to an exemplary embodiment of the invention particle size effects on assembly. Two types of particles can be assembled into complementary patterns according to their size. Particles with large size (e.g., 500 μm) are assembled on the antinodes while particles with small size (e.g., 100 μm) are assembled on the nodal regions.
Figure 11A:
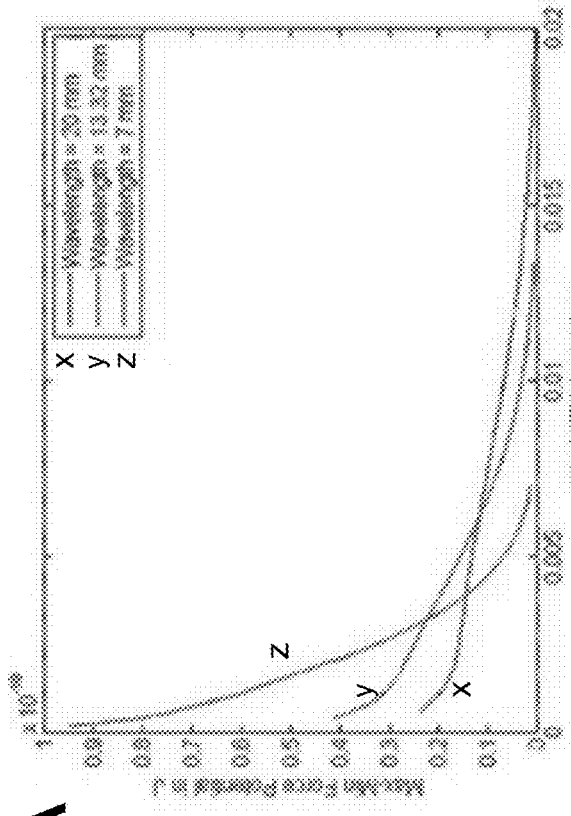
FIGS. 11A-B show according to an exemplary embodiment of the invention a frequency effect on the assembly.
Figure 11B:
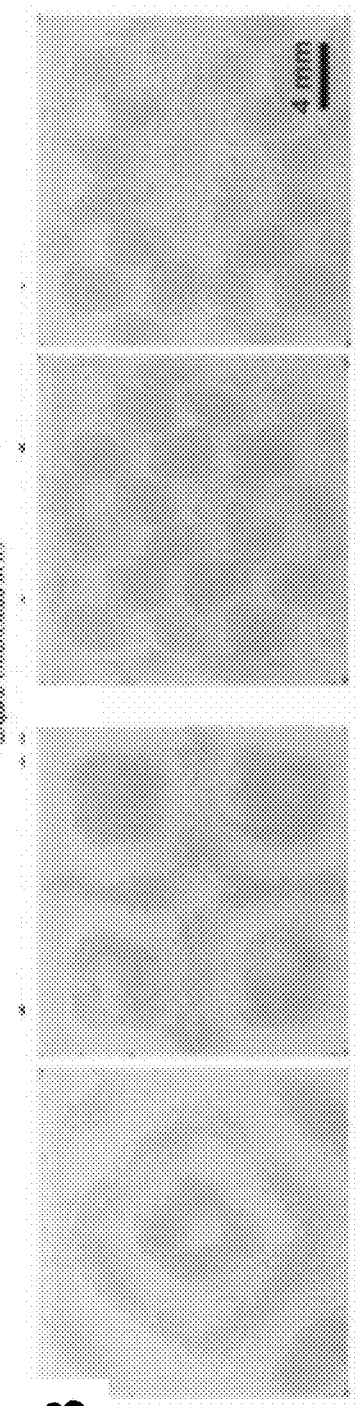
Figure 13:
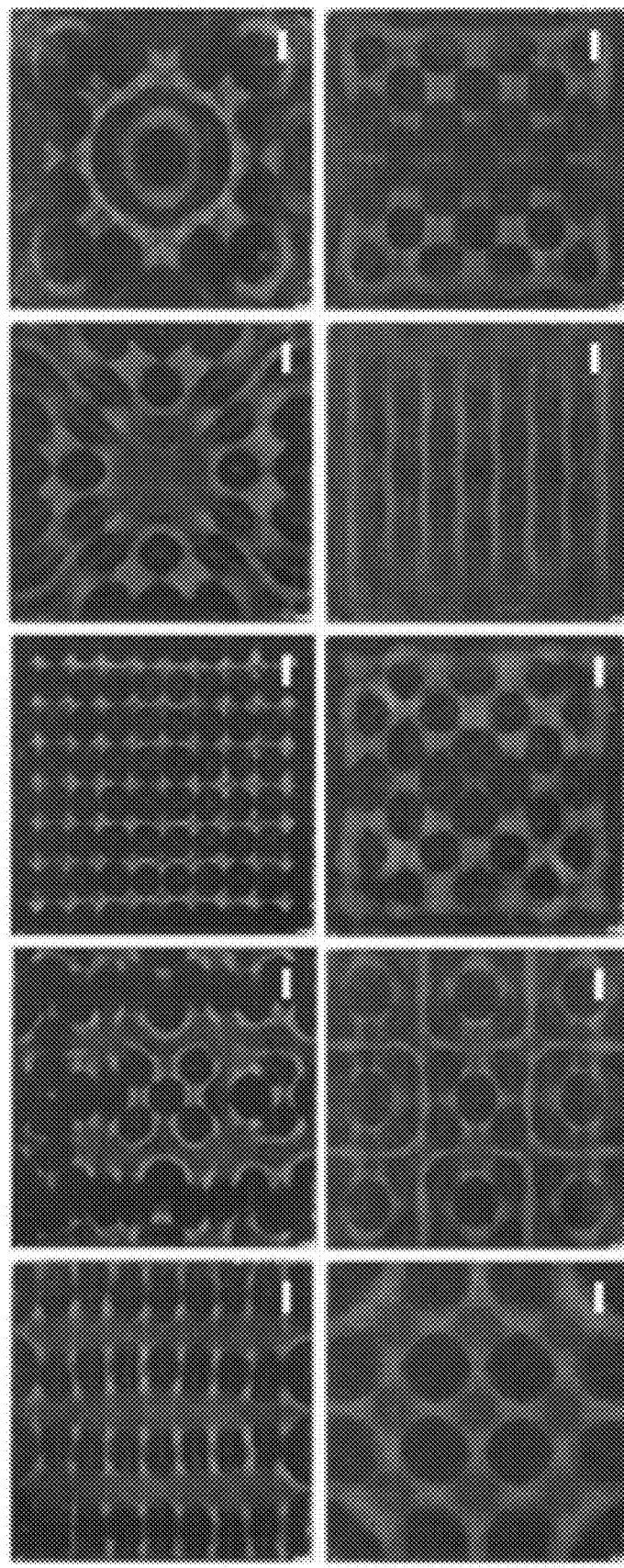
FIG. 13 shows according to an exemplary embodiment of the invention an assembly of hepatocytes. Three-dimensional scaffold-free cell assembly by hydrodynamic drag force have been created by Faraday waves. Assembly of hepatocytes into various patterns on the substrate of the liquid-carrier chamber by adjusting frequency of Faraday waves. 0.5 M hepatocytes are used in the assembly. Scale-bar=2 mm.
Figure 17:
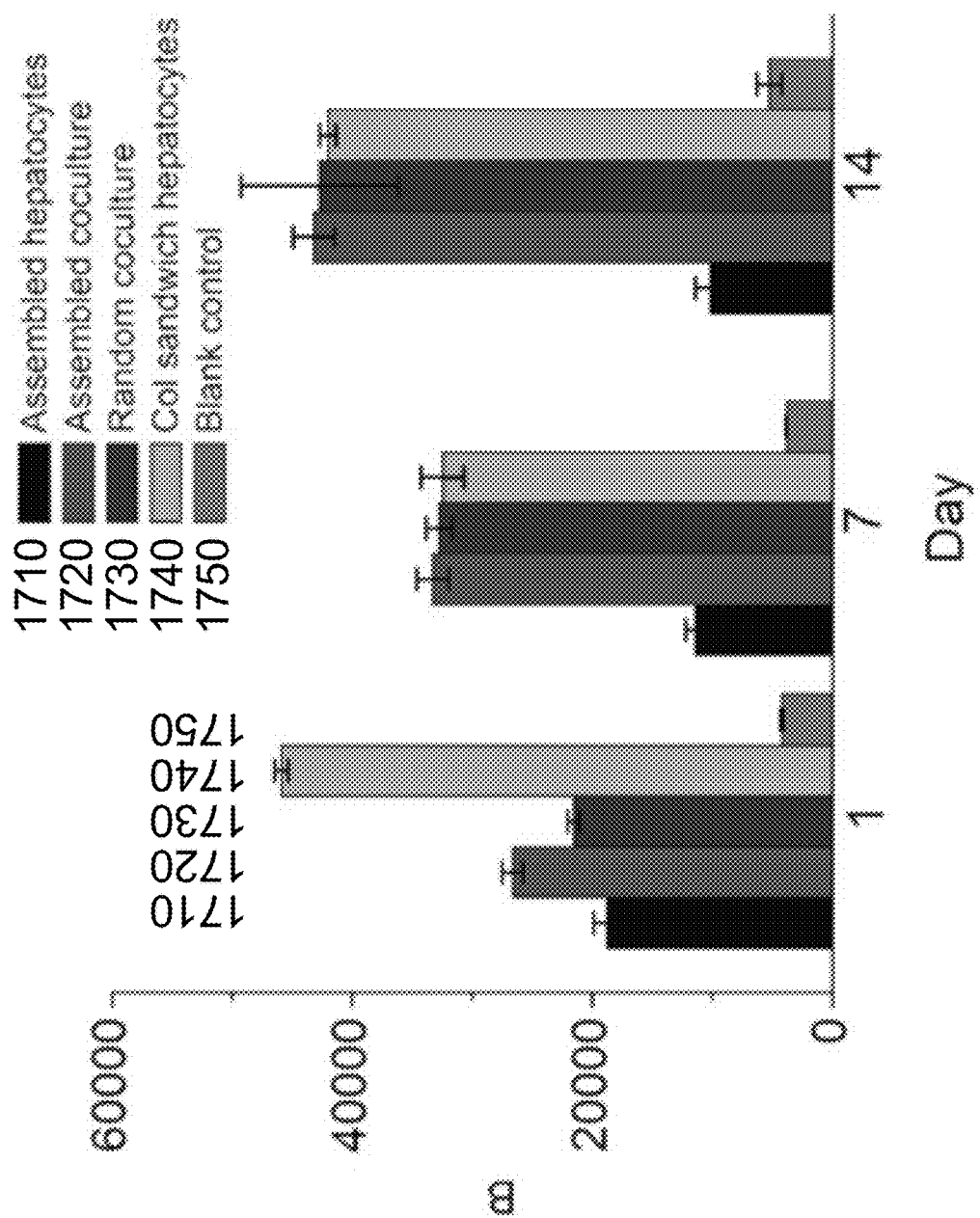
FIG. 17 shows according to an exemplary embodiment of the invention cell viability: PrestoBlue assays—PrestoBlue assays in day 1, 7 and 14. Incubation 2 hours. n=6. PrestoBlue assays indicate hepatocyte viability. Col sandwich hepatocytes indicate positive control group using collagen sandwich method.
Figure 18:
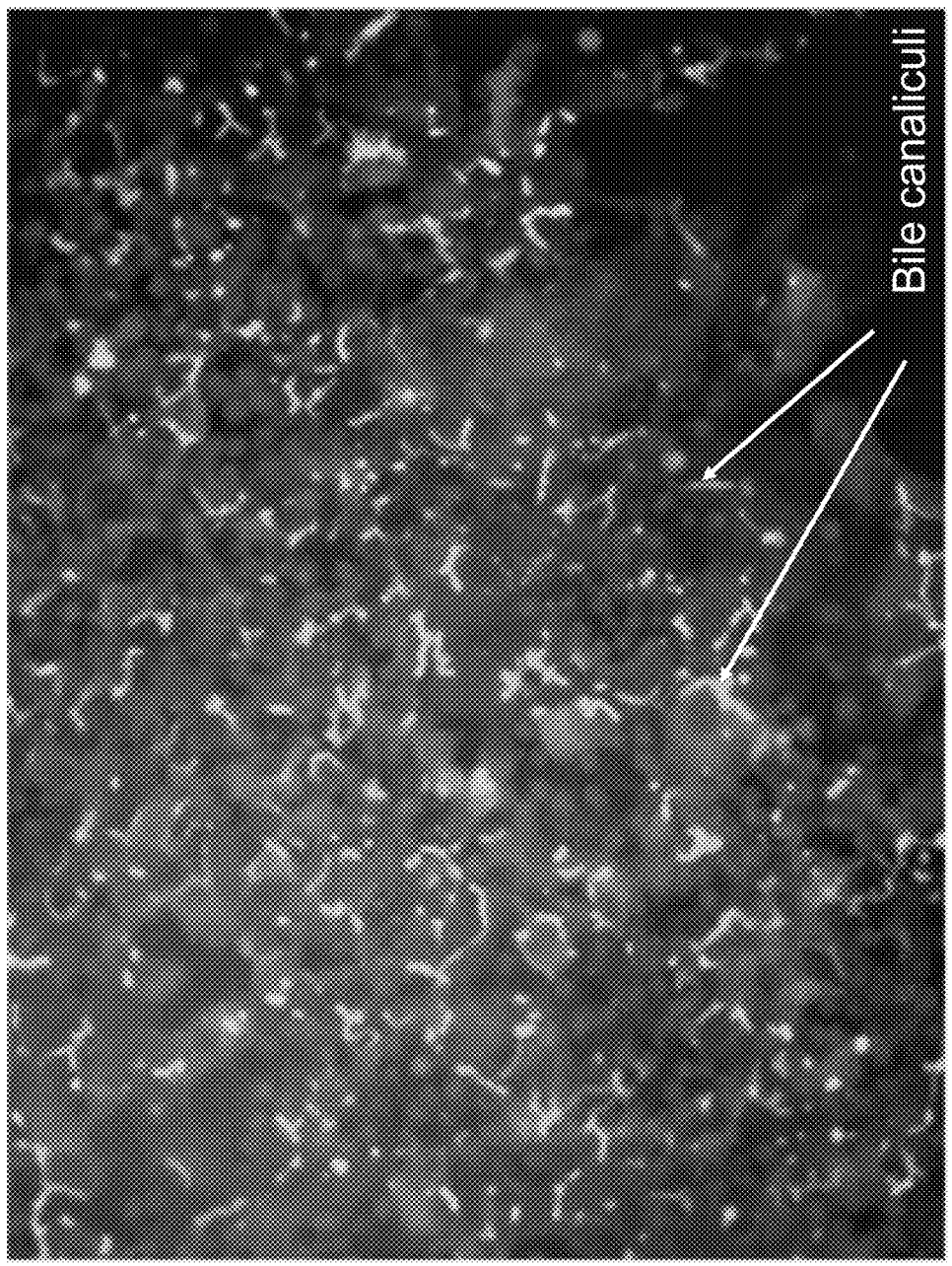
FIG. 18 shows according to an exemplary embodiment of the invention bile canaliculi staining, which was performed in the sixth day. Bright green (shown in grey scale) indicates formation of bile canaliculi in bioengineered liver tissues. Bile canaliculus is a thin tube that collects bile secreted by hepatocytes. The bile canaliculi merge and form bile ductules, which eventually become common hepatic duct.
Figures 19A, 19B:
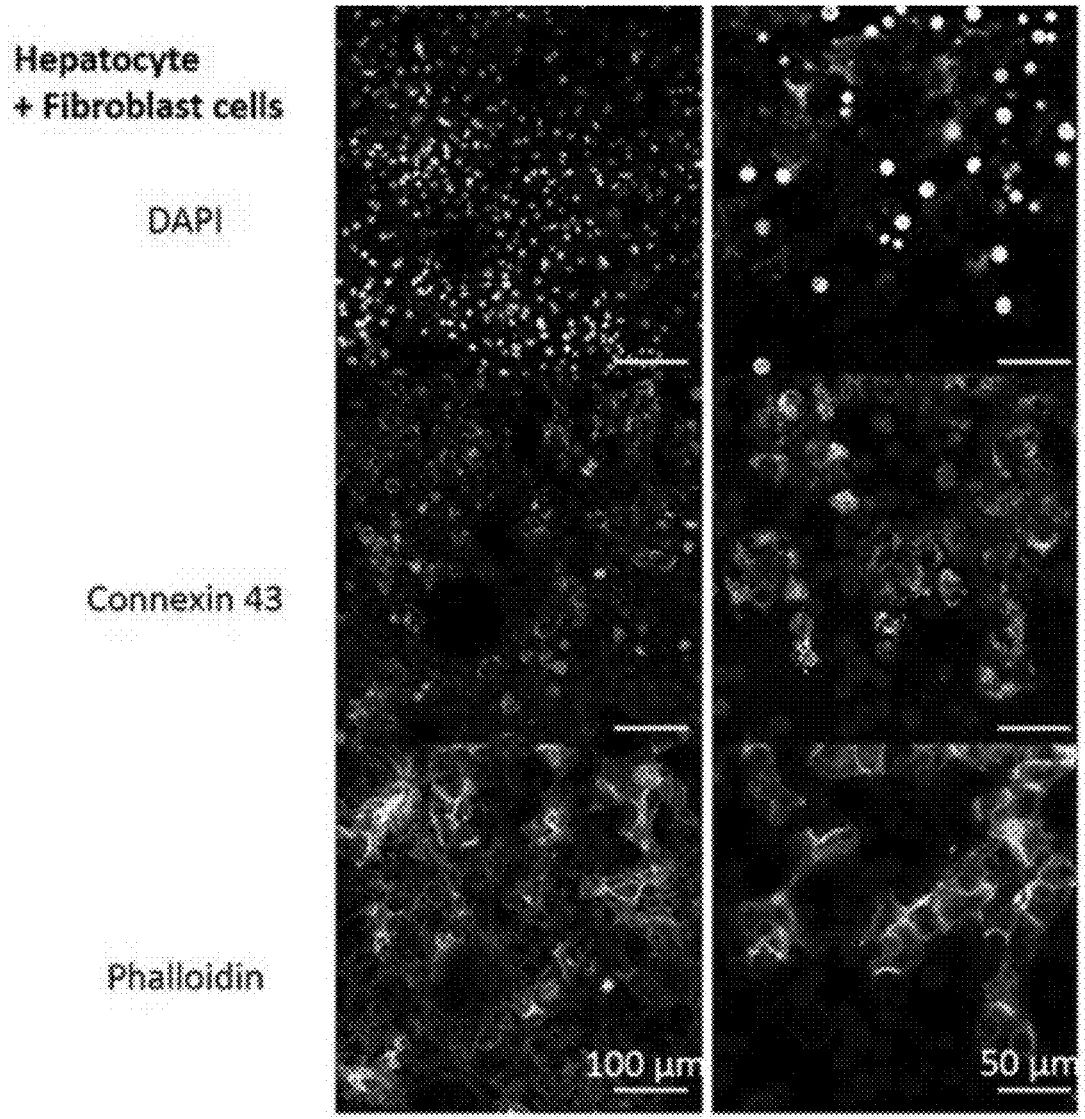
FIGS. 19A-B show according to an exemplary embodiment of the invention connexin staining. 3 M hepatocytes and 0.5 M 3T3 mouse fibroblast cells were assembled. Staining was performed in the third day. Connexins, or gap junction proteins, are a family of structurally related transmembrane proteins that assemble to form vertebrate gap junctions.
Figure 20:
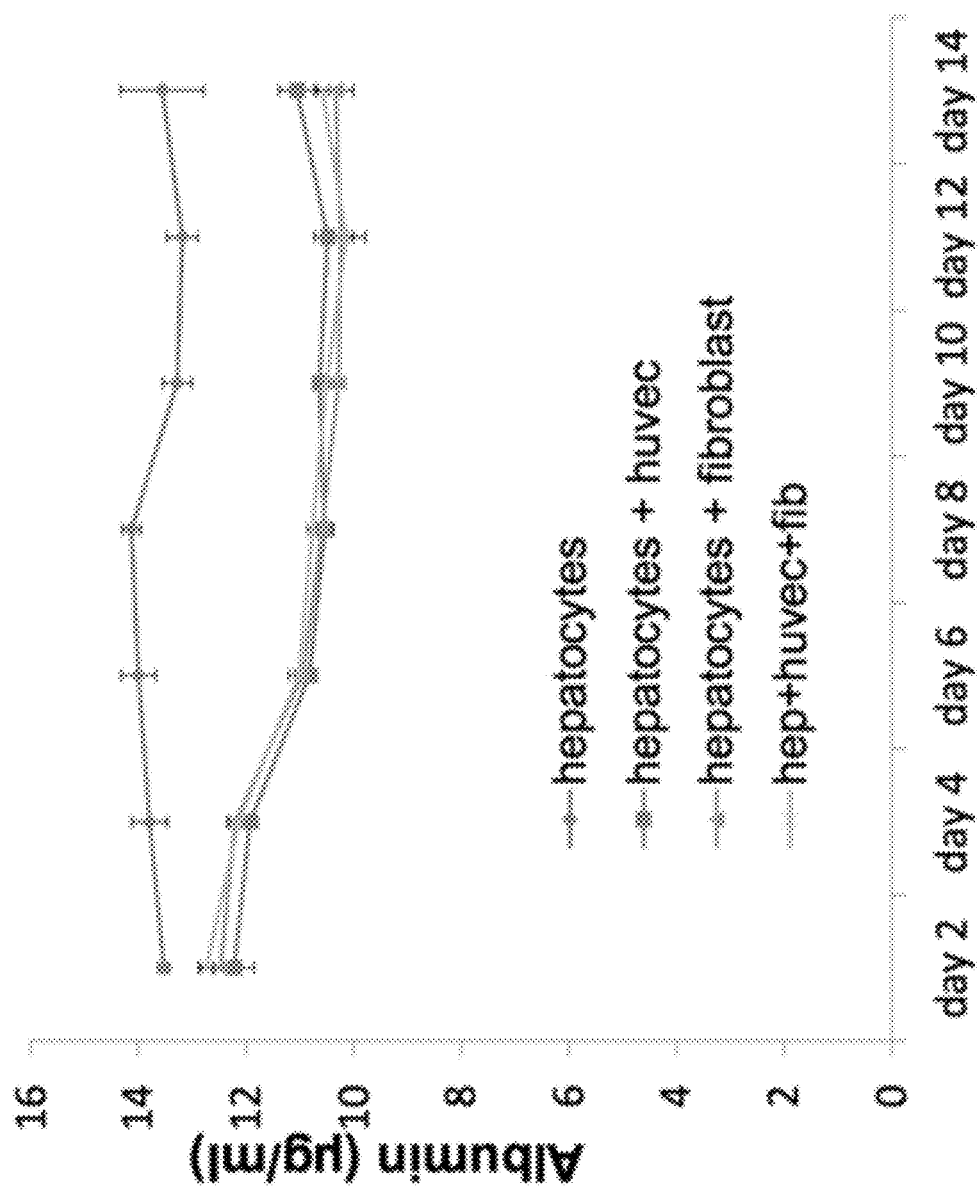
FIG. 20 shows according to an exemplary embodiment of the invention liver functional validation: albumin secretion assays—Albumin secretion (n=3). Results indicated function formation of hepatocytes in the engineered liver tissue.
Figure 21:
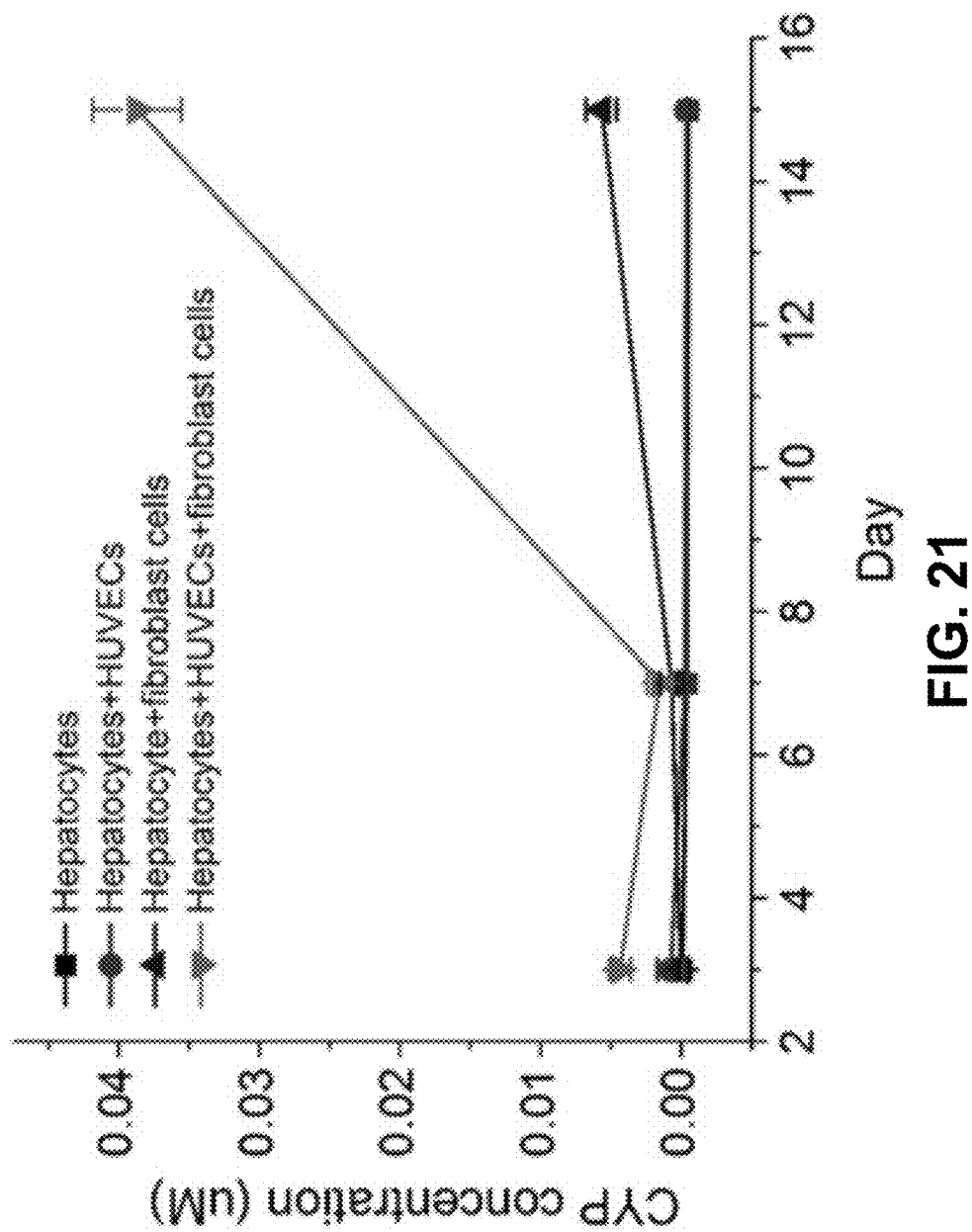
FIG. 21 shows according to an exemplary embodiment of the invention cytochrome P450 (CYP) assays-day 3, 7 and 15, n=3. Human CYPs are primarily membrane-associated proteins. Cytochrome P450 enzymes function to metabolize potentially toxic compounds, including drugs and products of endogenous metabolism such as bilirubin, principally in the liver. CYP assays indicated function formation of hepatocytes in the engineered liver tissue in the coculture microenvironment.
Figure 22:
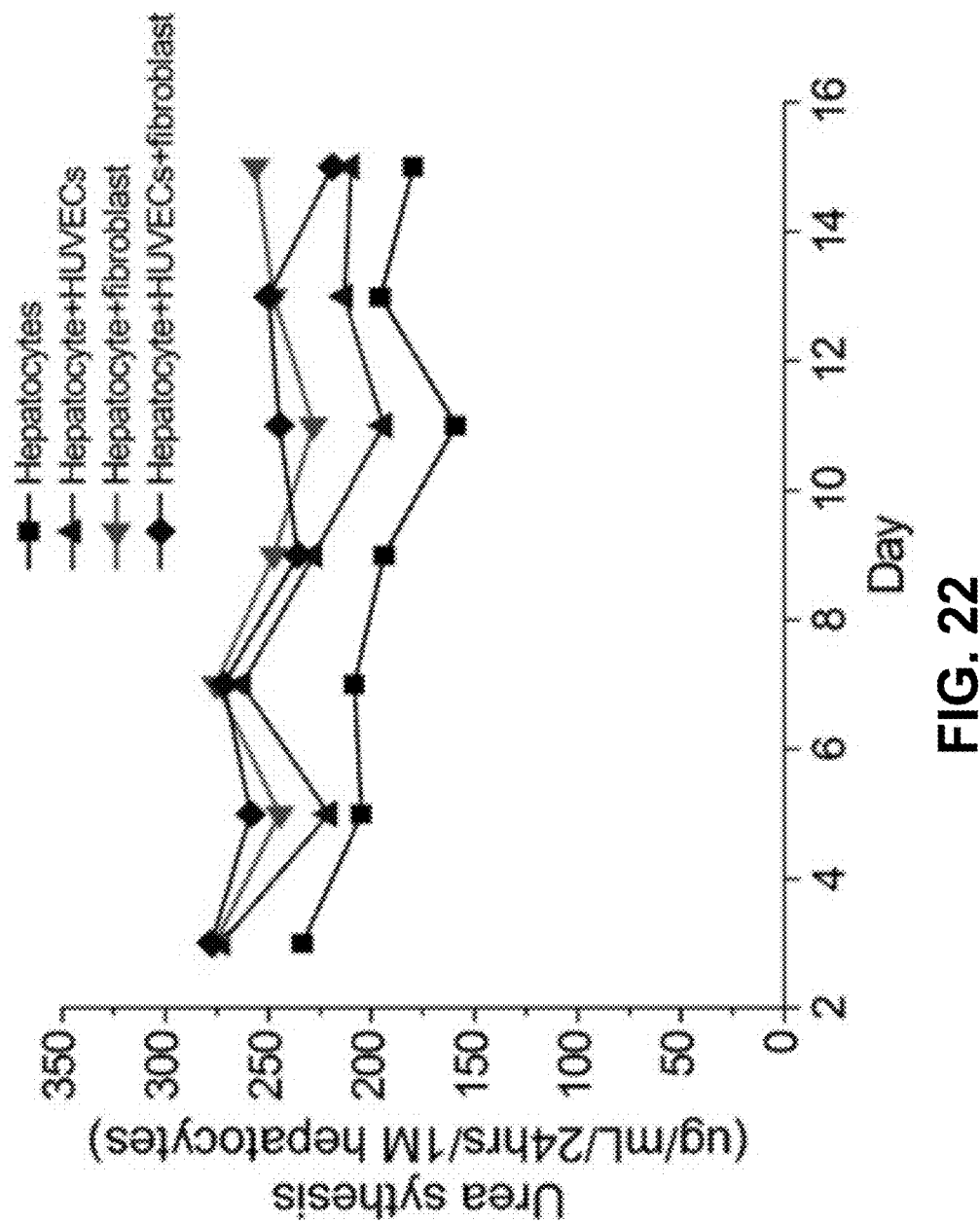
FIG. 22 shows according to an exemplary embodiment of the invention human urea synthesis assays from day 3 to day 15, n=3. Urea production is another hepatic specific parameter of functional hepatocytes. This parameter is characteristic of their detoxification performance.
Figure 23:
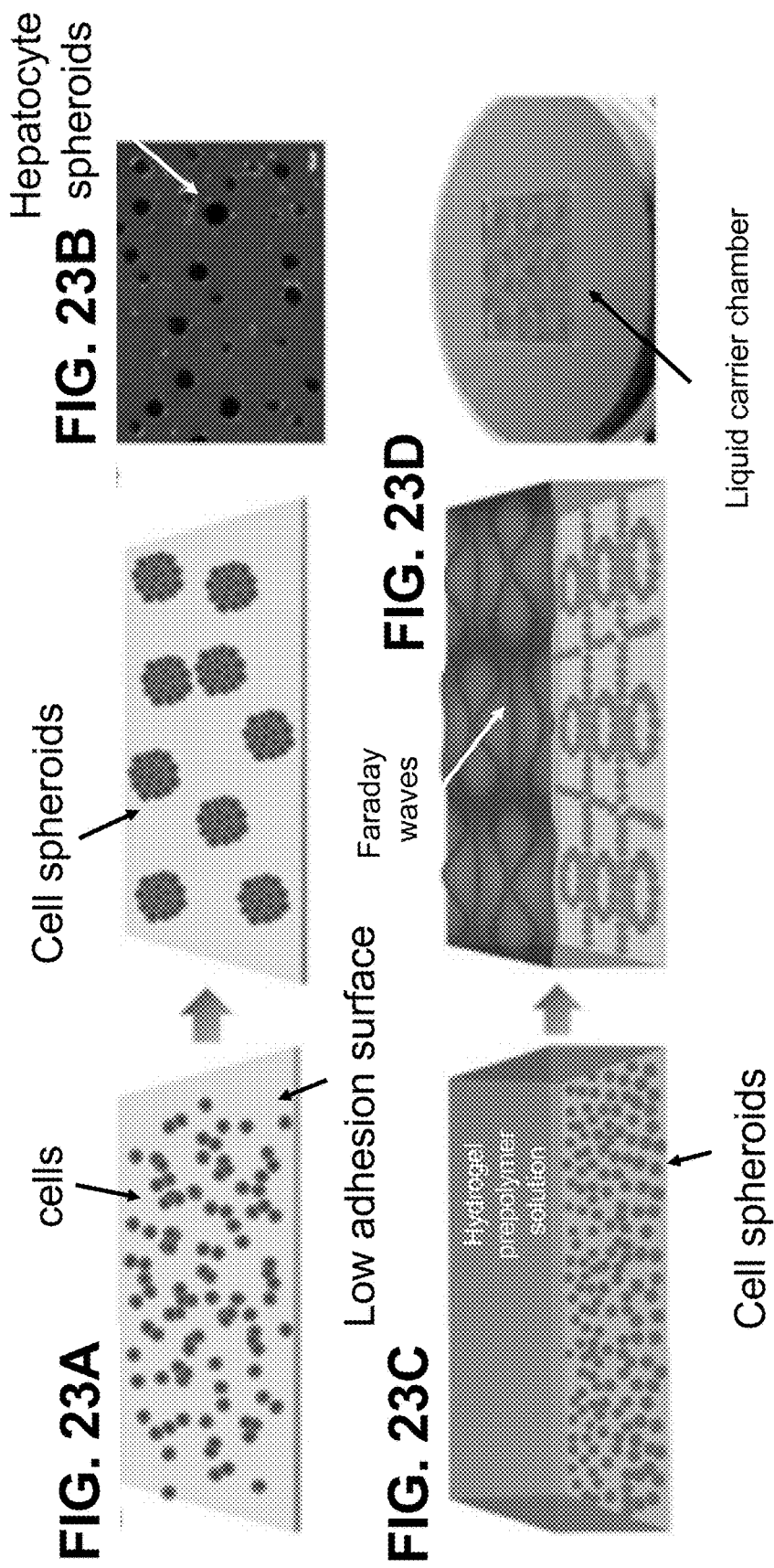
FIGS. 23A-D show according to an exemplary embodiment of the invention schematic demonstration of assembly technology and spheroid formation.
Figure 24:
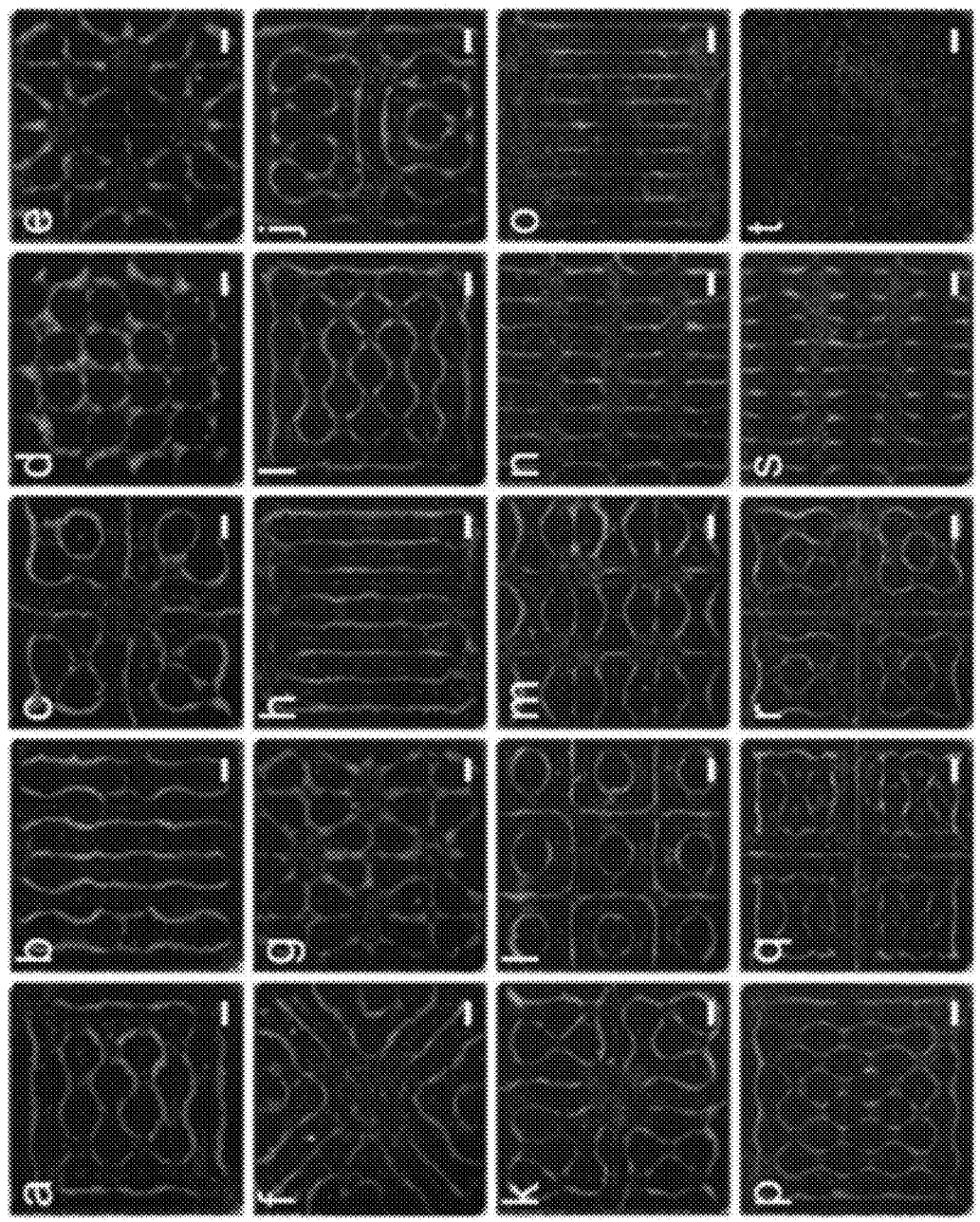
Figure 25:
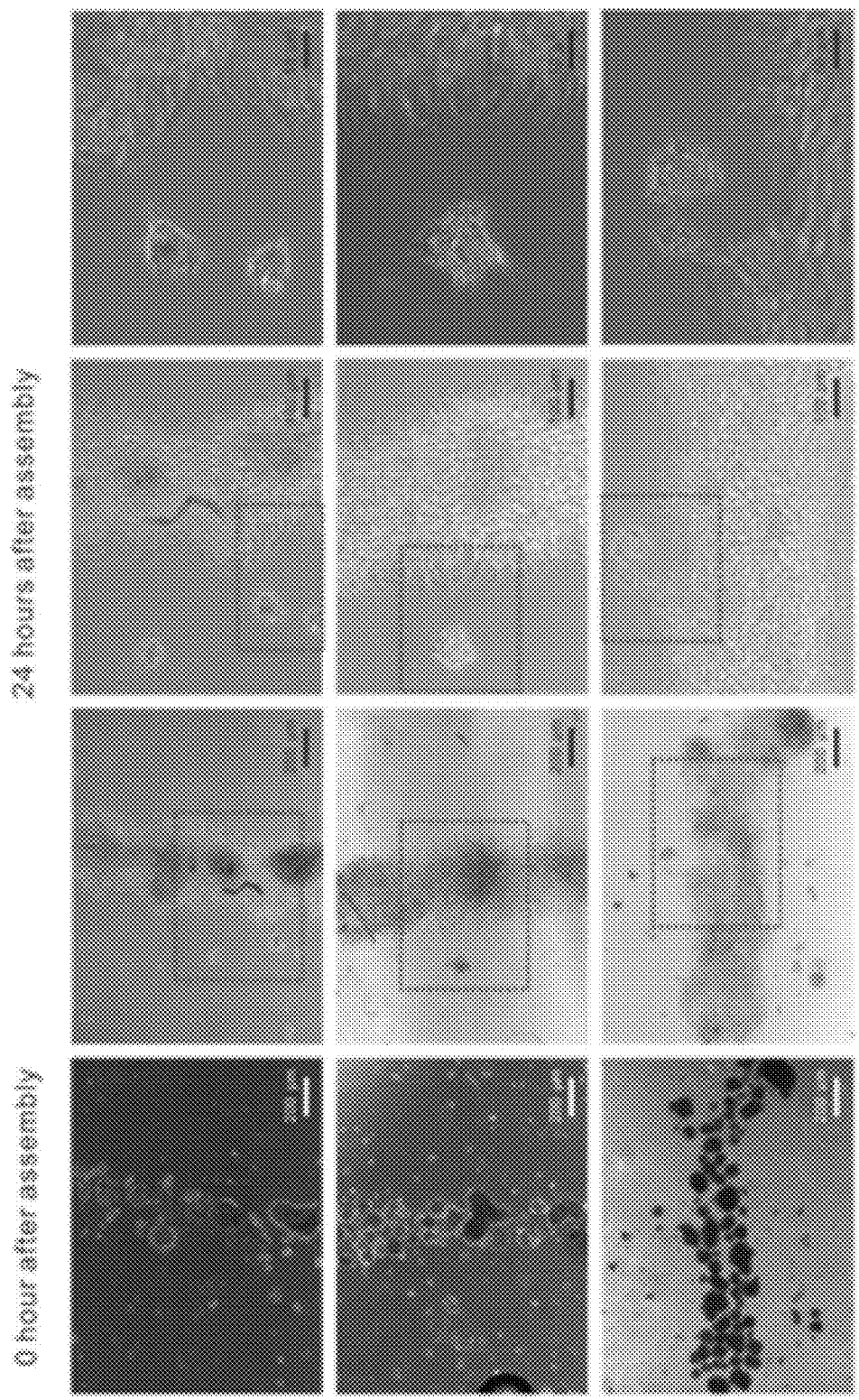
FIG. 25 shows according to an exemplary embodiment of the invention an assembly of fibroblast spheroids (Cell line with high proliferation capability). Patterned fibroblast spheroids are immobilized in 20 mg mL$^{-1}$ fibrinogen (500 µL) mixed with 0.625 IU mL$^{-1}$ thrombin (180 µL). Gelation was completed within 15 min and transferred into 30 mm Petri dish supplemented with cell culture medium. Cell spheroids fused into 3D microtissues after 24 hours.

As shown in FIG. 1, a vibration generator (U56001, 3B Scientific, Tucker, Ga.), driven by an audio amplifier (Lepai LP-2020A+, Parts Express, Ohio) and a function generator (HP 8116A, Hewlett-Packard GmbH, Germany), was used to generate vertical vibration. The vertical vibrational acceleration was monitored by an accelerometer (MMA7341L, Freescale Semiconductor, Tex.). The vibration generator was fixed on a metric tilt platform (Edmund Optics, N.J.), which was used to adjust the level of the chamber using a bubble level (Spirit Level, Hoefer, Mass.) as a reference. The metric tilt platform was fixed to a vibration damper (McMaster-Carr, Ga.) to prevent external perturbation. Liquid-carrier chambers can be multiple well plate, Petri dish, Transwell plate or any other commercialized standard cell culture containers or customized containers. The chamber was mounted on the top of the vibration generator using an adapter fitting. The thickness of liquid layer should be less than half wavelength of applied Faraday waves. The density of liquid should be smaller than buoyant density of samples to allow samples sink down to the substrate of the liquid carrier chamber. Faraday waves can be generated at the liquid surface by vertical vibration of a liquid layer using vibration generator. Formation of Faraday waves will generate a patterned velocity field, which will further generate a hydrodynamic shear stress on the substrate of the liquid carrier chamber.

Assembly Pattern Design

To design the tissue structure you want to generate, a physical model is used to calculate the corresponding geometry of the liquid carrier chamber, vibrational frequency and acceleration for this tissue structure. The following exemplary procedure could be used:

(1) Prepare cells. Harvest cells from native tissue, or maintained cell lines.
(2) Prepare cell suspension solution. Re-suspend one or more types of cells in cell culture medium with designed cell concentration and ratio. The cell concentration is correlated to the thickness of the generated tissue.
(3) Load cell suspension solution into the liquid-carrier chamber. Wait till all the cells gravitationally settle down to the substrate of the liquid-carrier chamber. Normally, it's take one minutes or more which is determined by liquid thickness, cell size and related density between cells and liquid and fluid viscosity.
(4) Applying hydrodynamic drag force. Turn on the vibration generator and apply calculated frequency and acceleration. Faraday waves are generated on the liquid surface as a result of hydrodynamic instability created by vertical vibration of the liquid layer. Faraday waves generate a patterned velocity field inside the liquid layer. This velocity field creates patterned hydrodynamic drag force on the cells on the substrate of the liquid-carrier chamber. Cells are dragged to the designed region and form multilayer structure. Cells with large size, buoyant density will be assembled under the antinodes of Faraday waves inside liquid while cells with small size and buoyant density will be assembled under the nodal region of Faraday waves inside liquid. Movement of cells can be predicted by the physical model as described herein. The number of layers are correlated to the number of the cells in the chamber. Assembly of cells can be completed by applying Faraday waves on the liquid surface for 5 to 10 seconds.
(5) Tissue culture of the assembled cell encapsulating construct. Transfer assembled cells to incubator for tissue culture. Culture assembled cells for one or more weeks with specific tissue culture medium based on the tissue type for formation of tissue functions.
(6) These functionalized tissues can be used for tissue-based drug screening or other tissue engineering applications.

Alternative building blocks can be cell spheroid, cell aggregates, or cell on the microcarriers and the following exemplary procedure could be used:

(1) Prepare cell spheroids. Prepare cell spheroids from harvest cells from native tissue, or maintained cell lines using commercially-available hanging drop techniques, low affinity plates or other techniques [1].
(2) Prepare cell spheroid solution. Re-suspend one or more types of cell spheroids in cell culture medium with desired number and ratio. The number of cell spheroids determines the thickness of the generated tissue.
(3) Load cell spheroid solution into the liquid-carrier chamber. Wait till all the cells gravitationally settle down to the substrate of the liquid-carrier chamber.
(4) Apply hydrodynamic drag force. Turn on the vibration generator and apply calculated frequency and acceleration. Faraday waves are generated on the liquid surface as a result of hydrodynamic instability created by vertical vibration of the liquid layer. Faraday waves generate a patterned velocity field inside the liquid layer. This velocity field creates hydrodynamic drag force on the cell spheroids on the substrate of the liquid-carrier chamber. Cell spheroids will be dragged to the designed region with multilayer structure based on their size and buoyant density. Cell spheroids with large size, buoyant density will be assembled under the antinodes of Faraday waves inside liquid while cell spheroids with small size and buoyant density will be assembled under the nodal region of Faraday waves inside liquid. Movement of cell spheroids can be predicted by the physical model developed by our team. The number of layers are determined by the number of the cell spheroids in the chamber. Assembly of cells can be completed by applying Faraday waves on the liquid surface for 5 to 10 seconds [6].

An alternative approach are developed to stabilize assembled cells and the following exemplary procedure could be used:

(1) Prepare hydrogel prepolymer solution. The hydrogel prepolymer solution can be derived from thermal crosslinking (e.g., Collagen), chemical crosslinking (e.g., fibrin) or photo crosslinking (e.g., methacrylated gelatin hydrogel) hydrogels.
(2) Prepare cell suspension solution. Resuspend one or more types of cells in hydrogel prepolymer solution with desired cell concentration and ratio. The cell concentration determines the thickness of the generated tissue.
(3) Load cell suspension solution into the liquid-carrier chamber. Wait till all the cells gravitationally settle down to the substrate of the liquid-carrier chamber.
(4) Apply hydrodynamic drag force. Turn on the vibration generator and apply calculated frequency and acceleration. Faraday waves are generated on the liquid surface as a result of hydrodynamic instability created by vertical vibration of the liquid layer. Faraday waves generate a patterned velocity field inside the liquid layer. This velocity field creates hydrodynamic drag force on the cells on the substrate of the liquid-carrier chamber. Cells will be dragged to the designed region with multilayer structure based on their size and buoyant density. Cells with large size, buoyant density will be assembled under the antinodes of Faraday waves inside liquid while cells with small size and buoyant density will be assembled under the nodal region of Faraday waves inside liquid. The number of layers are determined by the number of the cells in the chamber. Assembly of cells can be completed by applying Faraday waves on the liquid surface for 5 to 10 seconds.
(5) Tissue culture. Transfer assembled cells in hydrogel for tissue culture. Culture assembled cells for one or more weeks with specific tissue culture medium based on the tissue type for formation of tissue functions.
(6) These functionalized tissues can be used for tissue-based drug screening or other tissue engineering applications.

Physical Model

A physical model to describe particle assembly inside the liquid has been developed. The particles on the substrate of the liquid-carrier chamber experience gravity, buoyant, hydrodynamic drag forces and normal force. The forces in vertical direction don't change particles distribution in x-y plane. The drag force in the x-y planes of liquid is proportional to their velocity fields in the liquid. The physical model of this velocity field created by Faraday waves has been developed previously [2-4] and can be expressed as below, $$u = \frac{2\omega h}{\sinh(kH)}$$

$$\begin{bmatrix} \left(\cos(\omega t) - e^{-\frac{z}{\delta}}\cos\left(\omega t - \frac{z}{\delta}\right)\right)\zeta_{sh} + \frac{4h}{L} \\ \left\{-\frac{3\pi}{8\sinh^3(kH)}\left[\sin(2\omega t) - e^{-\frac{\sqrt{2}z}{\delta}}\sin\left(2\omega t - \sqrt{2}\frac{z}{\delta}\right)\right]\zeta_{h'} + \right. \\ \frac{\pi\sin(2\omega t)}{4\sinh(kH)}\left[e^{-\frac{\sqrt{2}}{\delta}}\cos\left(\frac{\sqrt{2}z}{\delta}\right) - e^{-\frac{z}{\delta}}\cos\left(\frac{z}{\delta}\right) + \right. \\ \frac{\sqrt{2}z}{\delta}e^{-\frac{z}{\delta}}\sin\left(\frac{z}{\delta} + \frac{\pi}{4}\right)\right]\zeta_h + \\ \frac{\pi\cos(2\omega t)}{4\sinh(kH)}\left[-e^{-\frac{\sqrt{2}}{\delta}}\sin\left(\frac{\sqrt{2}z}{\delta}\right) + \right. \\ \left. e^{-\frac{z}{\delta}}\sin\left(\frac{z}{\delta}\right) + \frac{\sqrt{2}z}{\delta}e^{-\frac{z}{\delta}}\cos\left(\frac{z}{\delta} + \frac{\pi}{4}\right)\right]\zeta_h + \\ \left. \frac{\pi}{8\sinh(kH)}\left[-3 + e^{-\frac{2z}{\delta}} + 8e^{-\frac{z}{\delta}}\sin\left(\frac{z}{\delta}\right) + 2e^{-\frac{z}{\delta}}\cos\left(\frac{z}{\delta}\right) - \right. \right. \\ \left. \left. 2\sqrt{2}\left(\frac{z}{\delta}\right)e^{-\frac{z}{\delta}}\cos\left(\frac{z}{\delta} + \frac{\pi}{4}\right)\right]\zeta_h \right\} \end{bmatrix}$$

where $\omega$ is the Faraday wave frequency, k is the Faraday wavenumber, h is the Faraday wave amplitude, H is the thickness of liquid, L is the length of liquid chamber, z is the distance from the point where wave is completely decayed, $\zeta_{sh}$ is the standing wave with sub-harmonic frequency ($\omega$), $\zeta_h$ is the standing wave with harmonic frequency ($2\omega$), $\zeta_{h'}$ is the standing wave with harmonic frequency ($2\omega$) with phase $\pi/2$ and $\delta$ is the Stokes characteristic length which is given by $$\delta = \sqrt{\frac{2v}{\omega}}$$

where v is the kinematic viscosity of the liquid.

For 3×3 ring pattern, $$\zeta_{sh} = (\cos(3k \cdot x) \cdot \cos(k \cdot y) - \cos(k \cdot x) \cdot \cos(3k \cdot y))$$

$$\zeta_h = (\cos(6k \cdot x) \cdot \cos(2k \cdot y) - \cos(2k \cdot x) \cdot \cos(6k \cdot y))$$

$$\zeta_{h'} = (\sin(6k \cdot x) \cdot \sin(2k \cdot y) - \sin(2k \cdot x) \cdot \sin(6k \cdot y))$$

The Stokes drag force is used to model the force drag equation.

$$F_{drag} = 6\pi v \rho_{liq} R(u_s - u)$$

where R is the radius of the particle, $\rho_{par}$ is the density of the particle, $\rho_{liq}$ is the density of liquid and $u_s$ is the settling velocity which is given by $$u_s = \frac{2}{9} \frac{(\rho_{par} - \rho_{liq})}{v \rho_{liq}} g R^2$$

To make the final expression for force potential independent of time before casting it in the form of minimization, the velocity field is time averaged. The time averaged drag force directed along x-y plane can be computed as follows:

$$<F_{drag}> = 6v\rho_{liq}R\omega \int_0^{T=\frac{\pi}{\omega}} (u_s - u)dt$$

Only a part of sub-harmonic component and the last term of harmonic component will sustain after time-averaging the velocity field.

$$<F_{drag}> = \begin{bmatrix} \frac{4}{3}(\rho_{par} - \rho_{liq})\omega g R^3 + \frac{24 v \rho_{liq} R \omega e^{\frac{z}{\delta}} \sin\left(\frac{z}{\delta}\right)}{\sinh(kH)} \zeta_{sh} - \\ \frac{6\pi^2 v \rho_{liq} R h \omega}{L(\sinh(kH))^2}\left\{-3 + e^{-\frac{2z}{\delta}} + \right. \\ 8 e^{-\frac{z}{\delta}} \sin\left(\frac{z}{\delta}\right) + 2 e^{-\frac{z}{\delta}} \cos\left(\frac{z}{\delta}\right) - \\ \left. 2\sqrt{2} \frac{z}{\delta} e^{-\frac{z}{\delta}} \cos\left(\frac{z}{\delta} + \frac{\pi}{4}\right)\right\}\zeta_h \end{bmatrix}$$

The final expression for the force potential is obtained from the relation, $F_{Drag} = -\nabla U$. Since, we are interested in the force potential at the bottom of liquid and also the decay length is $\lambda/2$ [5], z is given by $$z = \frac{\lambda}{2} - H$$

$$U_{drift} = \begin{bmatrix} -\frac{4}{3}(\rho_{par} - \rho_{liq})\omega g R^3 - \frac{24 v \rho_{liq} R \omega e^{-\left(\frac{\lambda}{2}-H\right)}\sin\left(\frac{\frac{\lambda}{2}-H}{\delta}\right)}{k \sinh(kH)} \zeta_{sh} + \\ \frac{3\pi^2 v \rho_{liq} R h \omega}{kL(\sinh(kH))^2}\left\{ \begin{array}{c} -3 + e^{-2\left(\frac{\lambda}{2}-H\right)/\delta} + 8 e^{-\left(\frac{\lambda}{2}-H\right)/\delta} \sin\left(\frac{\frac{\lambda}{2}-H}{\delta}\right) \\ + 2 e^{-\left(\frac{\lambda}{2}-H\right)/\delta} \cos\left(\frac{\frac{\lambda}{2}-H}{\delta}\right) \\ -2\sqrt{2}\left(\frac{\frac{\lambda}{2}-H}{\delta}\right) e^{-\left(\frac{\lambda}{2}-H\right)/\delta} \cos\left(\frac{\frac{\lambda}{2}-H}{\delta} + \frac{\pi}{4}\right) \end{array} \right\}\zeta_h \end{bmatrix}$$

Particles in the fluid will fill the bottom of the liquid-carrier chamber from the region with the lowest force potential to the region with the highest force potential. We developed this equation above, which can be used to predict assembly and pattern formation inside liquid. Using this equation, we can design assembly of cells, cell spheroids or any other biological entities on the nodal regions or antinode region of Faraday waves by tuning parameters such as particle size, particle density, liquid density and excitation frequency. Two cell types or biological entities can be assembled into complementary patterns by varying their buoyant densities and sizes. Assembly of materials with complementary patterns can benefit many application such as studying cell-to-cell interactions, cell-biomaterials interaction and cell-biochemical interaction.

[1] Asghar, W. et al. in *Cancer Targeted Drug Delivery* (eds You Han Bae, Randall J. Mrsny, & Kinam Park) Ch. 24, 635-665 (Springer N.Y., 2013).

[2] Lin, C., Jeng, D. S. & Jeng, C. N. An experimental study on the flow characteristics of a standing wave: application of FLDV measurements. *Ocean Engineering* 29, 1265-1282, doi:http://dx.doi.org/10.1016/S0029-8018(01)00067-1 (2002).

[3] Miche, R. *Mouvements ondulatoires de la mer en profondeur constante ou decroissante forme limite de la houle lors de son deferlement, application aux digues maritimes.* (1944).

[4] Noda, H. A STUDY ON MASS TRANSPORT IN BOUNDARY LAYERS IN STANDING WAVES. *Coastal Engineering Proceedings; No* 11 (1968): *Proceedings of* 11*th Conference on Coastal Engineering, London, United Kingdom,* 1968.

[5] Anthoni, J. F. *Oceanography: waves theory and principles of waves, how they work and what causes them,* <http://www.seafriends.org.nz/oceano/waves.htm> (2000).

[6] Chen, P. et al., Biotunable Acoustic Node Assembly of Organoids, Advanced Healthcare Materials 2015, 4 (13): 1937-43.

What is claimed is:

1. A method of making a multi-layer patterned cell assembly, comprising:
   (a) providing a liquid-carrier chamber defining a bottom of the chamber;
   (b) loading a cell suspension liquid solution containing cells into the liquid-carrier chamber and letting the cells in the cell suspension liquid solution settle down to the bottom of the chamber;
   (c) determining that the cells in the cell suspension liquid solution have gravitationally settled down to the bottom of the chamber; and
   (d) applying a hydrodynamic drag force by using a vibration generator with a frequency and acceleration to the cells which have settled at the bottom of the chamber, whereby the frequency and acceleration are designed to drag the settled cells into a three-dimensional pattern to form a multi-layer three-dimensional patterned cell assembly.

2. The method as set forth in claim 1, further comprising transferring the formed multi-layer three-dimensional patterned cell assembly from the liquid-carrier chamber to an incubator to form a tissue culture.

3. The method as set forth in claim 2, further comprising using the tissue culture for tissue-based drug screening or a tissue engineering application.

4. The method as set forth in claim 1, wherein the frequency is defined in a range of 1 Hz to 10,000 Hz and the acceleration is defined in a range of 0.01 $m/s^2$ to 5000 $m/s^2$.

5. The method as set forth in claim 1, wherein two types of cells are assembled into complementary patterns according to their size within the multi-layer three-dimensional patterned cell assembly.

\* \* \* \* \*